(12) United States Patent
Chang et al.

(10) Patent No.: US 9,140,704 B2
(45) Date of Patent: *Sep. 22, 2015

(54) SERUM MARKERS ASSOCIATED WITH EARLY AND OTHER STAGES OF BREAST CANCER

(75) Inventors: Frank N. Chang, Dresher, PA (US); Phu T. Duong, Malvern, PA (US); George P. Tuszynski, Pittsgrove, NJ (US)

(73) Assignee: Temple University of The Commonwealth System of Higher Education, Philadelphia, PA (US)

( * ) Notice: Subject to any disclaimer, the term of this patent is extended or adjusted under 35 U.S.C. 154(b) by 790 days.

This patent is subject to a terminal disclaimer.

(21) Appl. No.: 13/384,014

(22) PCT Filed: Jul. 13, 2010

(86) PCT No.: PCT/US2010/041813
§ 371 (c)(1),
(2), (4) Date: Mar. 27, 2012

(87) PCT Pub. No.: WO2011/008746
PCT Pub. Date: Jan. 20, 2011

(65) Prior Publication Data
US 2012/0183555 A1    Jul. 19, 2012

Related U.S. Application Data

(63) Continuation-in-part of application No. 12/670,343, filed as application No. PCT/US2008/000509 on Jan. 15, 2008, now Pat. No. 8,333,880.

(60) Provisional application No. 60/962,081, filed on Jul. 26, 2007, provisional application No. 61/225,254, filed on Jul. 14, 2009.

(51) Int. Cl.
| | | |
|---|---|---|
| *G01N 1/00* | (2006.01) |
| *G01N 33/00* | (2006.01) |
| *G01N 33/48* | (2006.01) |
| *G01N 33/53* | (2006.01) |
| *G01N 33/574* | (2006.01) |
| *C07K 14/47* | (2006.01) |
| *C07K 16/30* | (2006.01) |
| *G01N 33/68* | (2006.01) |

(52) U.S. Cl.
CPC ...... *G01N 33/57415* (2013.01); *C07K 14/4748* (2013.01); *C07K 16/3015* (2013.01); *G01N 33/57488* (2013.01); *G01N 33/68* (2013.01); *G01N 2333/765* (2013.01); *G01N 2550/00* (2013.01); *G01N 2800/56* (2013.01)

(58) Field of Classification Search
CPC . G01N 1/00; G01N 2800/00; G01N 2800/56; G01N 33/00; G01N 33/48; G01N 33/53; G01N 33/574; G01N 33/57407; G01N 33/57415; G01N 33/57423; G01N 33/57438; G01N 33/57484; G01N 33/57488; G01N 33/68; G01N 33/6863; G01N 33/3693
See application file for complete search history.

(56) References Cited

U.S. PATENT DOCUMENTS

| | | |
|---|---|---|
| 3,930,973 A | 1/1976 | Nerenberg |
| 3,984,298 A | 10/1976 | Haber |
| 4,128,470 A | 12/1978 | Hiratsuka |
| 4,146,454 A | 3/1979 | Haber |
| 4,892,814 A | 1/1990 | Harrington |
| 4,909,918 A | 3/1990 | Bambeck |
| 5,068,019 A | 11/1991 | Yoshida |
| 5,137,609 A | 8/1992 | Manian |
| 5,264,098 A | 11/1993 | Chevigne |
| 5,314,595 A | 5/1994 | Fuller |
| 5,637,202 A | 6/1997 | Harrington |
| 6,528,640 B1 | 3/2003 | Beigelman |
| 6,855,554 B2 | 2/2005 | Fritsche |
| 6,939,424 B1 | 9/2005 | Takala et al. |
| 7,326,326 B2 | 2/2008 | Chang et al. |
| 7,575,858 B2 | 8/2009 | Yonan |
| 2004/0121488 A1 | 6/2004 | Chang |
| 2004/0142862 A1 | 7/2004 | Whistler et al. |
| 2006/0068452 A1 | 3/2006 | Goldknopf |
| 2006/0266715 A1* | 11/2006 | Loewy ..................... 210/787 |
| 2007/0161030 A1 | 7/2007 | Patton |
| 2009/0023149 A1 | 1/2009 | Knudsen |
| 2009/0234202 A1 | 9/2009 | Goix et al. |

(Continued)

FOREIGN PATENT DOCUMENTS

| | | |
|---|---|---|
| JP | 0613033 | 5/1994 |
| JP | 63262550 | 10/1998 |

(Continued)

OTHER PUBLICATIONS

M. Schuchard et al. "Comparison of Precipitation Methods Following Depletion of Twenty High Abundance Proteins from Human Plasma", 3 pages, publically available Jan. 11, 2006.*

(Continued)

*Primary Examiner* — Alana Harris Dent

(74) *Attorney, Agent, or Firm* — RatnerPrestia

(57) ABSTRACT

Methods for identifying disease-specific markers, in particular breast cancer markers, by electrophoretically separating serum albumin complexes in a biological sample on a membrane are provided. Electrophoretic separation profiles representing different diseases or different cancer stages can be produced, and used in the diagnosis, prognosis and treatment of these diseases. Methods for identification of a cancer peptide fragment comprising a cancer peptide motif are provided. Also provided are breast cancer and other cancer markers and antibodies that specifically recognize these markers.

13 Claims, 15 Drawing Sheets

(56) References Cited

U.S. PATENT DOCUMENTS

| | | |
|---|---|---|
| 2011/0031122 A1 | 2/2011 | Chang et al. |
| 2011/0287450 A1 | 11/2011 | Bottaro et al. |
| 2012/0039811 A1* | 2/2012 | Admon et al. ............ 424/9.1 |

FOREIGN PATENT DOCUMENTS

| | | |
|---|---|---|
| WO | WO 01/65262 A2 | 9/2001 |
| WO | WO 03/031942 A1 | 4/2003 |
| WO | 03044485 | 5/2003 |
| WO | WO 03/056341 A2 | 7/2003 |
| WO | WO 2004/052290 A2 | 6/2004 |
| WO | WO 2005/118856 A1 | 12/2005 |
| WO | WO 2006/125195 A2 | 11/2006 |
| WO | WO 2008/031064 A1 | 3/2008 |
| WO | WO 2008/079269 A2 | 7/2008 |
| WO | WO 2009/014552 A1 | 1/2009 |
| WO | WO 2011/008746 A2 | 1/2011 |

OTHER PUBLICATIONS

Sjovall et al. (Gynecologic Oncology 85: 175-178, 2002).*
International Search Report and Written Opinion issued by the Korean Intellectual Property Office for International Application No. PCT/US2013/039430, Jul. 22, 2013.
Zheng, et al., Experimental and Molecular Pathology, 93:111-15 (2012).
Tuszynski et al., Experimental and Molecular Pathology, 91:608-13 (2011).
Bordier, J. Biol. Chem., 256:1604-07 (1981).
Dennis et al., J. Biol. Chem., 277:35035-43 (2002).
Gallent et al., Methods Mol. Biol., 421:53-60 (2008).
Ghimenti et al., Breast Cancer Res., 2(Suppl 1):P1.15 (2000) (Excerpt).
Graff et al., Cancer Research, 68:631-34 (2008).
Hosaka et al., Cancer Sci, 97:623-32 (2006).
Kim et al., Breast Cancer Research, 11:R22 1-12 (2009).
Lowenthal et al., Clinical Chemistry, 51:1933-45 (2005).
Lowrie et al., Brit. J. Cancer, 94:1663-71 (2006).
O'Farrel et al., J. Biol. Chem., 250:4007-21 (1974).
Porter et al., Proc. Natl. Acad. Sci., 100:10931-36 (2003).
Rini, Clinical Cancer Research, 14:1286-90 (2008).
Sonora et al., J Histochem Cytochem, 54:289-99 (2006).
Kohwi-Shigematsu, The Medical News, 1-4 (2008).
Vonderhaar, Endocrine-Related Cancer, 6:389-404 (1999).
Wirtenberger et al., Carcinogenesis, 27:593-98 (2006).
Yonan et al., Anal. Biochemistry, 338:159-61 (2005).
Database Geneseq [Online] XP002607581, Accession No. GSP:ADP83402 (2004).
Database Geneseq [Online] XP002607582, Accession No. GSP:ADP83499 (2004).
Database Geneseq [Online] XP002607583, Accession No. GSP:ADP83500 (2004).
Database Geneseq [Online] XP002607584, Accession No. GSP:ADP83400 (2004).
Database Geneseq [Online] XP002607585, Accession No. GSP:ADP83502 (2004).
Database Geneseq [Online] XP002607586, Accession No. GSP:ADP83501 (2004).
Database Geneseq [Online] XP002607587, Accession No. GSP:ADV60477 (2005).
PCT/US2010/041813 International Search Report by Marco Montrone dated Nov. 2, 2011.
Michael Lederer, "An Introduction to Paper Electrophoresis and Related Methods," Elsevier Publishing Company, 1955, pp. 17-30.
Allen, et al., International Journal of Pharmaceutics 187 (1999), pp. 259-272.
Norman Haber, Biotechnic & Histochemistry, vol. 73, No. 2, Feb. 1998, pp. 59-69 (Abstract Only).
Norman Haber, Proc. Natl. Acad. Sci. USA, Biochemistry, vol. 79, Jan. 1982, pp. 272-276.
Heller et al., Electrophoresis 1993, vol. 14, pp. 162-164.
Database Geneseq [Online] XP002720903, Accession No. GSP:AAE11228 (2001).
Database Geneseq [Online] XP002720904, Accession No. GSP:ARL91745 (2008).
Devine et al., Breast Cancer Research and Treatment, vol. 34, 3:241-51 (1995).
Hollingsworth et al., Nature Reviews, vol. 4, 1:45-60 (2004) (Excerpt).
Price et al., Eur. J. Cancer Clinical Oncology, vol. 24, 12:1799-1804 (1988).
EP 13 18 8276 Partial European Search Report by Thomas Kania dated Feb. 26, 2014.
Ariazl et al., "Estrogen Receptors as Therapeutic Targets in Breast CAncer", Current Topics in Medicinal Chemistry, 6(3), 181-202 (2006) (Abstrtact).
Barton, "Commercial Opportunities from Blomarkers Transforming Drug Discovery, Clinical Development and Molecular Diagnostic", Business Insights Ltd., 5 pages (2006), Only Table of Contents.
Filardo at al., Endocrinology, 148(7):3236-45 (2007).
Gasparini et al., Critical Reviews in Oncology/Hematology, 57(1):79-101 (2006).
Yeon and Pegram, Investogational New Drugs, 23:391-409 (2005).
Ariazi et al., "Estrogen Receptors as Therapeutic Targets in Breast Cancer", Current Topics in Medicinal Chemistry, 6(3), 181-202 (2006) (Abstract).
Barton, "Commercial Opportunities from Biomarkers Transforming Drug Discovery, Clinical Development and Molecular Diagnostic", Business Insights Ltd., 5 pages (2006).
Baselga et al., Science, 312:1175-78 (2006).
Corthals et al., Electrophoresis, 21:1104-15 (2000).
Druker, Advances in Cancer Research, 91:1-30 (2004).
Duffy, Clinical Chemistry, 51(3):494-503 (2005).
Filardo et al., Endocrinology, 148(7):3236-45 (2007).
Gasparini et al., Critical Reviews in Oncology/Hemtology, 57(1):79-101 (2006).
Hayes, Breast, 14(6):493-99 (2005).
He et al., Proteomics, 5:3442-53 (2005).
Merrell et al., J. Biomol. Tech., 15(4):238-48 (2004).
Moser et al., Pharmacology, 86:22-29 (2010).
Notification of Transmittal of the International Search Report and the Written Opinion of the International Searching Authority, or the Declaration issued for International Application No. PCT/US2013/039430 by Seung Beam Kim, mailed Jul. 23, 2013.
O'Farrell, J. Biol. Chem 250(10):4007-21 (1975).
Ryberg et al., British J. Pharmacol., 152:1092-1101 (2007).
Simonin et al., J. Neurochem., 89:766-75 (2004).
Thomas and Dong, J. Steroid Biochem and Molr Biol., 102:175-79 (2006).
Whistler et al., Science, 297:615-20 (2002).
Yeon and Pegram, Investigational New Drugs, 23:391-409 (2005).

* cited by examiner

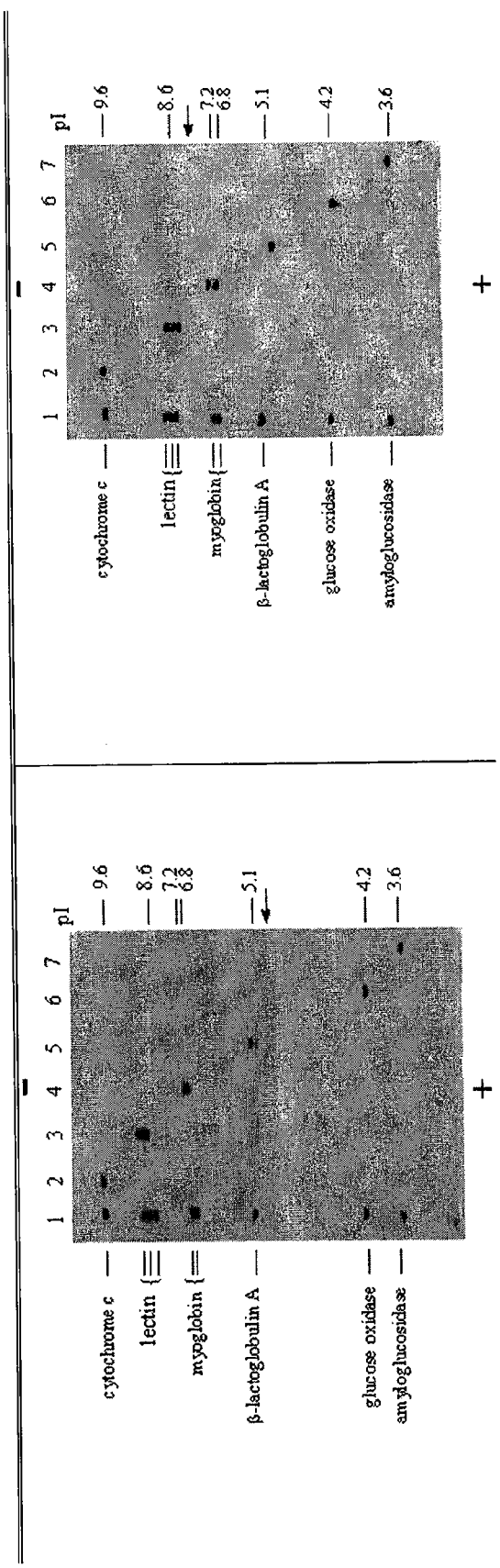

Normal Brain          Giant Cell Glioma

Adapted from Raybiotech, Inc.

SEQUENCE LISTING

<160> NUMBER OF SEQ ID NOS: 127

<210> SEQ ID NO 1
<211> LENGTH: 12
<212> TYPE: PRT

```
<213> ORGANISM: Artificial Sequence
<220> FEATURE:
<223> OTHER INFORMATION: Completely Synthesized

<400> SEQUENCE: 1

Thr Val Gln Ile Ala Ala Val Val Asp Val Ile Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Completely Synthesized

<400> SEQUENCE: 2

Phe Tyr Thr Ile Glu Ile Leu Lys Val Glu
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Completely Synthesized

<400> SEQUENCE: 3

Val Gly Pro Val Ser Leu Pro Arg
1               5

<210> SEQ ID NO 4
<211> LENGTH: 7
<212> TYPE: PRT
<213> ORGANISM: Artificial Sequence
<220> FEATURE:
<223> OTHER INFORMATION: Completely Synthesized

<400> SEQUENCE: 4

Ala Thr Glu Glu Gln Leu Lys
1               5

<210> SEQ ID NO 5
<211> LENGTH: 6
<212> TYPE: PRT
<213> ORGANISM: Artificial Sequence
<220> FEATURE:
<223> OTHER INFORMATION: Completely Synthesized

<400> SEQUENCE: 5

Thr Pro Val Ser Glu Lys
1               5

<210> SEQ ID NO 6
<211> LENGTH: 9
<212> TYPE: PRT
<213> ORGANISM: Artificial Sequence
<220> FEATURE:
<223> OTHER INFORMATION: Completely Synthesized

<400> SEQUENCE: 6

Trp Val Gly Asp Leu Pro Asn Gly Arg
1               5

<210> SEQ ID NO 7
<211> LENGTH: 6
<212> TYPE: PRT
<213> ORGANISM: Artificial Sequence
```

```
<220> FEATURE:
<223> OTHER INFORMATION: Completely Synthesized

<400> SEQUENCE: 7

Asp Asp Glu Lys Leu Lys
1               5

<210> SEQ ID NO 8
<211> LENGTH: 6
<212> TYPE: PRT
<213> ORGANISM: Artificial Sequence
<220> FEATURE:
<223> OTHER INFORMATION: Completely Synthesized

<400> SEQUENCE: 8

Ile Asp Ser Glu Ile Lys
1               5

<210> SEQ ID NO 9
<211> LENGTH: 11
<212> TYPE: PRT
<213> ORGANISM: Artificial Sequence
<220> FEATURE:
<223> OTHER INFORMATION: Completely Synthesized

<400> SEQUENCE: 9

Glu Asn Ala Gly Glu Asp Pro Gly Leu Ala Arg
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Completely Synthesized

<400> SEQUENCE: 10

Leu Gly Lys Asp Ala Val Glu Asp Leu Glu Ser Val Gly Lys
1               5                   10

<210> SEQ ID NO 11
<211> LENGTH: 6
<212> TYPE: PRT
<213> ORGANISM: Artificial Sequence
<220> FEATURE:
<223> OTHER INFORMATION: Completely Synthesized

<400> SEQUENCE: 11

Ile Tyr Glu Ile Ala Arg
1               5

<210> SEQ ID NO 12
<211> LENGTH: 9
<212> TYPE: PRT
<213> ORGANISM: Artificial Sequence
<220> FEATURE:
<223> OTHER INFORMATION: Completely Synthesized

<400> SEQUENCE: 12

Thr Thr Pro Thr Val Ile Ser Trp Lys
1               5

<210> SEQ ID NO 13
<211> LENGTH: 6
<212> TYPE: PRT
<213> ORGANISM: Artificial Sequence
<220> FEATURE:
```

```
<223> OTHER INFORMATION: Completely Synthesized

<400> SEQUENCE: 13

Ile Val Glu Val Ser Arg
1               5

<210> SEQ ID NO 14
<211> LENGTH: 16
<212> TYPE: PRT
<213> ORGANISM: Artificial Sequence
<220> FEATURE:
<223> OTHER INFORMATION: Completely Synthesized

<400> SEQUENCE: 14

Glu Met Asn Leu Glu Gly Thr Asn Leu Asp Lys Leu Pro Met Ala Ser
1               5                  10                  15

<210> SEQ ID NO 15
<211> LENGTH: 22
<212> TYPE: PRT
<213> ORGANISM: Artificial Sequence
<220> FEATURE:
<223> OTHER INFORMATION: Completely Synthesized

<400> SEQUENCE: 15

Thr Glu Gly Val Ser Val Ala Asp Arg Glu Ala Ser Leu Glu Leu Ile
1               5                  10                  15

Lys Leu Asp Ile Ser Arg
            20

<210> SEQ ID NO 16
<211> LENGTH: 11
<212> TYPE: PRT
<213> ORGANISM: Artificial Sequence
<220> FEATURE:
<223> OTHER INFORMATION: Completely Synthesized

<400> SEQUENCE: 16

Leu Glu Glu Leu Asp Leu Ala Ile Tyr Asn Ser
1               5                  10

<210> SEQ ID NO 17
<211> LENGTH: 6
<212> TYPE: PRT
<213> ORGANISM: Artificial Sequence
<220> FEATURE:
<223> OTHER INFORMATION: Completely Synthesized

<400> SEQUENCE: 17

Asn Leu Ser Leu Asn Ser
1               5

<210> SEQ ID NO 18
<211> LENGTH: 7
<212> TYPE: PRT
<213> ORGANISM: Artificial Sequence
<220> FEATURE:
<223> OTHER INFORMATION: Completely Synthesized

<400> SEQUENCE: 18

Leu Ser Gln Lys Phe Pro Lys
1               5

<210> SEQ ID NO 19
<211> LENGTH: 11
<212> TYPE: PRT
```

```
<213> ORGANISM: Artificial Sequence
<220> FEATURE:
<223> OTHER INFORMATION: Completely Synthesized

<400> SEQUENCE: 19

Leu Ser Ser Ser Ser Val Pro Ser Ala Asp Arg
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Completely Synthesized

<400> SEQUENCE: 20

Gln Gly Leu Pro Gly Thr Ser Asn Ser Asn Ser Ser Arg Ser Gly Ser
1               5                   10                  15

Gln Arg

<210> SEQ ID NO 21
<211> LENGTH: 8
<212> TYPE: PRT
<213> ORGANISM: Artificial Sequence
<220> FEATURE:
<223> OTHER INFORMATION: Completely Synthesized

<400> SEQUENCE: 21

Thr Tyr Thr Pro Glu Val Thr Lys
1               5

<210> SEQ ID NO 22
<211> LENGTH: 8
<212> TYPE: PRT
<213> ORGANISM: Artificial Sequence
<220> FEATURE:
<223> OTHER INFORMATION: Completely Synthesized

<400> SEQUENCE: 22

Leu Ala Glu Val Ser Pro Leu Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Completely Synthesized

<400> SEQUENCE: 23

Asp Ser Glu Gly Thr Pro Val Asn Lys
1               5

<210> SEQ ID NO 24
<211> LENGTH: 16
<212> TYPE: PRT
<213> ORGANISM: Artificial Sequence
<220> FEATURE:
<223> OTHER INFORMATION: Completely Synthesized

<400> SEQUENCE: 24

Gly Pro Tyr Glu Ser Gly Ser Gly His Ser Ser Gly Leu Gly His Arg
1               5                   10                  15

<210> SEQ ID NO 25
<211> LENGTH: 10
```

```
<212> TYPE: PRT
<213> ORGANISM: Artificial Sequence
<220> FEATURE:
<223> OTHER INFORMATION: Completely Synthesized

<400> SEQUENCE: 25

Leu Ala Gly Val Ala Gln Met Ser Ile Arg
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Completely Synthesized

<400> SEQUENCE: 26

Leu Pro Gly Ile Val Ala Glu Gly Arg
1               5

<210> SEQ ID NO 27
<211> LENGTH: 11
<212> TYPE: PRT
<213> ORGANISM: Artificial Sequence
<220> FEATURE:
<223> OTHER INFORMATION: Completely Synthesized

<400> SEQUENCE: 27

Asp Ala Val Glu Asp Leu Glu Ser Val Gly Lys
1               5                   10

<210> SEQ ID NO 28
<211> LENGTH: 23
<212> TYPE: PRT
<213> ORGANISM: Artificial Sequence
<220> FEATURE:
<223> OTHER INFORMATION: Completely Synthesized

<400> SEQUENCE: 28

Tyr Asp Pro Glu Ala Ala Ser Ala Pro Gly Ser Gly Asn Pro Cys His
1               5                   10                  15

Glu Ala Ser Ala Ala Gln Lys
            20

<210> SEQ ID NO 29
<211> LENGTH: 13
<212> TYPE: PRT
<213> ORGANISM: Artificial Sequence
<220> FEATURE:
<223> OTHER INFORMATION: Completely Synthesized

<400> SEQUENCE: 29

Gly Ala Val His Asp Val Lys Asp Val Leu Asp Ser Val
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Completely Synthesized

<400> SEQUENCE: 30

Asn Leu Ser Leu Asn Ser
1               5
```

```
<210> SEQ ID NO 31
<211> LENGTH: 7
<212> TYPE: PRT
<213> ORGANISM: Artificial Sequence
<220> FEATURE:
<223> OTHER INFORMATION: Completely Synthesized

<400> SEQUENCE: 31

Phe Glu Val Glu Val Thr Lys
1               5

<210> SEQ ID NO 32
<211> LENGTH: 23
<212> TYPE: PRT
<213> ORGANISM: Artificial Sequence
<220> FEATURE:
<223> OTHER INFORMATION: Completely Synthesized

<400> SEQUENCE: 32

Thr Arg Glu Leu Glu Glu Ile Ser Gln Gln Lys Asn Ala Ala Lys Asp
1               5                   10                  15

Asn Ser Leu Asp Thr Glu Val
            20

<210> SEQ ID NO 33
<211> LENGTH: 11
<212> TYPE: PRT
<213> ORGANISM: Artificial Sequence
<220> FEATURE:
<223> OTHER INFORMATION: Completely Synthesized

<400> SEQUENCE: 33

Gly Leu Ser Val Asp Ser Ala Gln Glu Val Lys
1               5                   10

<210> SEQ ID NO 34
<211> LENGTH: 18
<212> TYPE: PRT
<213> ORGANISM: Artificial Sequence
<220> FEATURE:
<223> OTHER INFORMATION: Completely Synthesized

<400> SEQUENCE: 34

Asp Ala Ile Asn Ala Glu Thr Val Leu Val Leu Val Asn Ala Val Tyr
1               5                   10                  15

Phe Lys

<210> SEQ ID NO 35
<211> LENGTH: 17
<212> TYPE: PRT
<213> ORGANISM: Artificial Sequence
<220> FEATURE:
<223> OTHER INFORMATION: Completely Synthesized

<400> SEQUENCE: 35

Asn Ile Phe Phe Ser Pro Leu Ser Leu Ser Ala Ala Leu Gly Met Val
1               5                   10                  15

Arg

<210> SEQ ID NO 36
<211> LENGTH: 15
<212> TYPE: PRT
<213> ORGANISM: Artificial Sequence
<220> FEATURE:
<223> OTHER INFORMATION: Completely Synthesized
```

```
<400> SEQUENCE: 36

Ile Gly Phe Ile Glu Glu Val Lys Ala Gln Ile Leu Glu Met Arg
1               5                   10                  15

<210> SEQ ID NO 37
<211> LENGTH: 7
<212> TYPE: PRT
<213> ORGANISM: Artificial Sequence
<220> FEATURE:
<223> OTHER INFORMATION: Completely Synthesized

<400> SEQUENCE: 37

Glu Glu Ile Ala Arg Gln Ala
1               5

<210> SEQ ID NO 38
<211> LENGTH: 14
<212> TYPE: PRT
<213> ORGANISM: Artificial Sequence
<220> FEATURE:
<223> OTHER INFORMATION: Completely Synthesized

<400> SEQUENCE: 38

Leu Ala Ile Leu Ser Gln Thr Glu Phe Tyr Glu Ala Leu Arg
1               5                   10

<210> SEQ ID NO 39
<211> LENGTH: 36
<212> TYPE: PRT
<213> ORGANISM: Artificial Sequence
<220> FEATURE:
<223> OTHER INFORMATION: Completely Synthesized

<400> SEQUENCE: 39

Phe Ile Ser Ala Ala Ala Val Pro Pro Gly Ser Leu Ser Gly Pro
1               5                   10                  15

Gly Leu Ala Pro Ala Ala Ser Ser Ala Gly Gly Ala Ser Ser Ala
            20                  25                  30

Gln Thr His Arg
        35

<210> SEQ ID NO 40
<211> LENGTH: 12
<212> TYPE: PRT
<213> ORGANISM: Artificial Sequence
<220> FEATURE:
<223> OTHER INFORMATION: Completely Synthesized

<400> SEQUENCE: 40

Lys Glu Asn Ala Gly Glu Asp Pro Gly Leu Ala Arg
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Completely Synthesized

<400> SEQUENCE: 41

Met Glu Asp Phe Val Thr Trp Val Asp Ser Ser Lys
1               5                   10

<210> SEQ ID NO 42
<211> LENGTH: 16
```

```
<212> TYPE: PRT
<213> ORGANISM: Artificial Sequence
<220> FEATURE:
<223> OTHER INFORMATION: Completely Synthesized

<400> SEQUENCE: 42

Ser Val Asn Glu Val Met Glu Trp Met Asn Asn Val Met Asn Ala Gln
1               5                   10                  15

<210> SEQ ID NO 43
<211> LENGTH: 8
<212> TYPE: PRT
<213> ORGANISM: Artificial Sequence
<220> FEATURE:
<223> OTHER INFORMATION: Completely Synthesized

<400> SEQUENCE: 43

Leu Ala Thr Ala Glu Leu Pro Arg
1               5

<210> SEQ ID NO 44
<211> LENGTH: 16
<212> TYPE: PRT
<213> ORGANISM: Artificial Sequence
<220> FEATURE:
<223> OTHER INFORMATION: Completely Synthesized

<400> SEQUENCE: 44

Glu Glu Ala Ser Pro Glu Ala Val Ala Gly Val Gly Phe Glu Ser Lys
1               5                   10                  15

<210> SEQ ID NO 45
<211> LENGTH: 14
<212> TYPE: PRT
<213> ORGANISM: Artificial Sequence
<220> FEATURE:
<223> OTHER INFORMATION: Completely Synthesized

<400> SEQUENCE: 45

Thr Glu Leu Ser Cys Thr Arg Gly Gly Cys Leu Ala Ser Arg
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Completely Synthesized

<400> SEQUENCE: 46

Asp Gly Glu Glu Lys Ile Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Completely Synthesized

<400> SEQUENCE: 47

Glu Gly Pro Ser Leu Gly Pro Pro Pro
1               5

<210> SEQ ID NO 48
<211> LENGTH: 20
<212> TYPE: PRT
```

```
<213> ORGANISM: Artificial Sequence
<220> FEATURE:
<223> OTHER INFORMATION: Completely Synthesized

<400> SEQUENCE: 48

Arg Gly Ala Pro Asp Pro Arg Val Asp Asp Ser Leu Gly Glu Phe
1               5                   10                  15

Pro Val Thr Asn
            20

<210> SEQ ID NO 49
<211> LENGTH: 11
<212> TYPE: PRT
<213> ORGANISM: Artificial Sequence
<220> FEATURE:
<223> OTHER INFORMATION: Completely Synthesized

<400> SEQUENCE: 49

Pro Lys Gly Gly Gly Tyr Ser Val Leu Ile Arg
1               5                   10

<210> SEQ ID NO 50
<211> LENGTH: 21
<212> TYPE: PRT
<213> ORGANISM: Artificial Sequence
<220> FEATURE:
<223> OTHER INFORMATION: Completely Synthesized

<400> SEQUENCE: 50

Gly Ala Asp Met Ile Ser Ile His Asn Glu Glu Glu Asn Ala Phe Ile
1               5                   10                  15

Leu Asp Thr Leu Lys
            20

<210> SEQ ID NO 51
<211> LENGTH: 15
<212> TYPE: PRT
<213> ORGANISM: Artificial Sequence
<220> FEATURE:
<223> OTHER INFORMATION: Completely Synthesized

<400> SEQUENCE: 51

Gly Pro Ala Leu Leu Val Leu Gly Pro Asp Ala Ile Gln Leu Arg
1               5                   10                  15

<210> SEQ ID NO 52
<211> LENGTH: 7
<212> TYPE: PRT
<213> ORGANISM: Artificial Sequence
<220> FEATURE:
<223> OTHER INFORMATION: Completely Synthesized

<400> SEQUENCE: 52

Phe Ala Pro Ser Val Val Gln
1               5

<210> SEQ ID NO 53
<211> LENGTH: 11
<212> TYPE: PRT
<213> ORGANISM: Artificial Sequence
<220> FEATURE:
<223> OTHER INFORMATION: Completely Synthesized

<400> SEQUENCE: 53

Asn Leu Ala Leu Cys Pro Ala Asn His Ala Pro
1               5                   10
```

<210> SEQ ID NO 54
<211> LENGTH: 14
<212> TYPE: PRT
<213> ORGANISM: Artificial Sequence
<220> FEATURE:
<223> OTHER INFORMATION: Completely Synthesized

<400> SEQUENCE: 54

Met Gln Asn Phe Leu Gln Leu Pro Glu Ala Glu Arg Asp Arg
1               5                   10

<210> SEQ ID NO 55
<211> LENGTH: 6
<212> TYPE: PRT
<213> ORGANISM: Artificial Sequence
<220> FEATURE:
<223> OTHER INFORMATION: Completely Synthesized

<400> SEQUENCE: 55

Asp Gly Glu Leu Cys Lys
1               5

<210> SEQ ID NO 56
<211> LENGTH: 12
<212> TYPE: PRT
<213> ORGANISM: Artificial Sequence
<220> FEATURE:
<223> OTHER INFORMATION: Completely Synthesized

<400> SEQUENCE: 56

Gln Ile Thr Asp Ser Ser Leu Gly Arg Ile Ala Gln
1               5                   10

<210> SEQ ID NO 57
<211> LENGTH: 9
<212> TYPE: PRT
<213> ORGANISM: Artificial Sequence
<220> FEATURE:
<223> OTHER INFORMATION: Completely Synthesized

<400> SEQUENCE: 57

Val Val Asp Gln Gly Cys Phe Pro Lys
1               5

<210> SEQ ID NO 58
<211> LENGTH: 27
<212> TYPE: PRT
<213> ORGANISM: Artificial Sequence
<220> FEATURE:
<223> OTHER INFORMATION: Completely Synthesized

<400> SEQUENCE: 58

Pro Asp Gly Ala Ser Cys Gln Gly Gln Pro Ala Leu His Ser Glu Asn
1               5                   10                  15

Pro Phe Ala Lys Ala Asn Gly Leu Pro Gly Lys
            20                  25

<210> SEQ ID NO 59
<211> LENGTH: 7
<212> TYPE: PRT
<213> ORGANISM: Artificial Sequence
<220> FEATURE:
<223> OTHER INFORMATION: Completely Synthesized

<400> SEQUENCE: 59

```
Glu Leu Ala Val Ile Leu Lys
1               5
```

<210> SEQ ID NO 60
<211> LENGTH: 18
<212> TYPE: PRT
<213> ORGANISM: Artificial Sequence
<220> FEATURE:
<223> OTHER INFORMATION: Completely Synthesized

<400> SEQUENCE: 60

```
Ala Ser Pro Ser Gly Asp Ala Ser Pro Pro Ala Thr Ala Pro Tyr Asp
1               5                   10                  15

Pro Arg
```

<210> SEQ ID NO 61
<211> LENGTH: 10
<212> TYPE: PRT
<213> ORGANISM: Artificial Sequence
<220> FEATURE:
<223> OTHER INFORMATION: Completely Synthesized

<400> SEQUENCE: 61

```
Ile Leu Gly Met Glu Gly Thr Ile Asp Arg
1               5                   10
```

<210> SEQ ID NO 62
<211> LENGTH: 31
<212> TYPE: PRT
<213> ORGANISM: Artificial Sequence
<220> FEATURE:
<223> OTHER INFORMATION: Completely Synthesized

<400> SEQUENCE: 62

```
Tyr Tyr Asp Gly Phe Met Gly Gln Arg Val Gly Ala Ile Ser Cys Leu
1               5                   10                  15

Ala Phe His Pro His Trp Pro His Leu Ala Val Gly Ser Asn Asp
            20                  25                  30
```

<210> SEQ ID NO 63
<211> LENGTH: 7
<212> TYPE: PRT
<213> ORGANISM: Artificial Sequence
<220> FEATURE:
<223> OTHER INFORMATION: Completely Synthesized

<400> SEQUENCE: 63

```
Leu Leu Ser Asp Leu Thr Lys
1               5
```

<210> SEQ ID NO 64
<211> LENGTH: 12
<212> TYPE: PRT
<213> ORGANISM: Artificial Sequence
<220> FEATURE:
<223> OTHER INFORMATION: Completely Synthesized

<400> SEQUENCE: 64

```
Asp Ala Gly Thr Glu Leu Thr Gly His Leu Val Pro
1               5                   10
```

<210> SEQ ID NO 65
<211> LENGTH: 12
<212> TYPE: PRT
<213> ORGANISM: Artificial Sequence
<220> FEATURE:

<223> OTHER INFORMATION: Completely Synthesized

<400> SEQUENCE: 65

Leu Gln Ala Gly Val Met Ala Ser Pro Pro Pro Pro
1               5                   10

<210> SEQ ID NO 66
<211> LENGTH: 9
<212> TYPE: PRT
<213> ORGANISM: Artificial Sequence
<220> FEATURE:
<223> OTHER INFORMATION: Completely Synthesized

<400> SEQUENCE: 66

Val Val Gly Pro Val Ser Leu Pro Arg
1               5

<210> SEQ ID NO 67
<211> LENGTH: 19
<212> TYPE: PRT
<213> ORGANISM: Artificial Sequence
<220> FEATURE:
<223> OTHER INFORMATION: Completely Synthesized

<400> SEQUENCE: 67

Gly Ala Pro Asp Pro Arg Val Asp Asp Ser Leu Gly Glu Phe Pro
1               5                   10                  15

Val Thr Asn

<210> SEQ ID NO 68
<211> LENGTH: 11
<212> TYPE: PRT
<213> ORGANISM: Artificial Sequence
<220> FEATURE:
<223> OTHER INFORMATION: Completely Synthesized

<400> SEQUENCE: 68

Gly Ile Leu Gly Met Glu Gly Thr Ile Asp Arg
1               5                   10

<210> SEQ ID NO 69
<211> LENGTH: 16
<212> TYPE: PRT
<213> ORGANISM: Artificial Sequence
<220> FEATURE:
<223> OTHER INFORMATION: Completely Synthesized

<400> SEQUENCE: 69

Val Ala Gln Gly Met Gly Ser Gly Ala His Thr Ala Asp Pro Glu Lys
1               5                   10                  15

<210> SEQ ID NO 70
<211> LENGTH: 24
<212> TYPE: PRT
<213> ORGANISM: Artificial Sequence
<220> FEATURE:
<223> OTHER INFORMATION: Completely Synthesized

<400> SEQUENCE: 70

Gly Ala Glu Val Asn Ala Val Thr Ser Asn Arg Ser Asp Pro Leu Lys
1               5                   10                  15

Asp Asp Pro His Met Ser Ser Asn
            20

<210> SEQ ID NO 71

```
<211> LENGTH: 8
<212> TYPE: PRT
<213> ORGANISM: Artificial Sequence
<220> FEATURE:
<223> OTHER INFORMATION: Completely Synthesized

<400> SEQUENCE: 71

Ile Ala Thr Ile Gly Ser Asp Arg
1               5

<210> SEQ ID NO 72
<211> LENGTH: 12
<212> TYPE: PRT
<213> ORGANISM: Artificial Sequence
<220> FEATURE:
<223> OTHER INFORMATION: Completely Synthesized

<400> SEQUENCE: 72

Ser Ser Gln Ser Ser Gln Pro Ser Arg Leu Leu Lys
1               5                   10

<210> SEQ ID NO 73
<211> LENGTH: 15
<212> TYPE: PRT
<213> ORGANISM: Artificial Sequence
<220> FEATURE:
<223> OTHER INFORMATION: Completely Synthesized

<400> SEQUENCE: 73

Asp Glu Glu Ser Leu Thr Val Cys Glu Asp Gly Cys Arg Asn Lys
1               5                   10                  15

<210> SEQ ID NO 74
<211> LENGTH: 19
<212> TYPE: PRT
<213> ORGANISM: Artificial Sequence
<220> FEATURE:
<223> OTHER INFORMATION: Completely Synthesized

<400> SEQUENCE: 74

Leu Phe Ala Ser Gly Asp Gln Val Phe Gln Val Pro Ile Gln Gly Pro
1               5                   10                  15

Gly Cys Arg

<210> SEQ ID NO 75
<211> LENGTH: 14
<212> TYPE: PRT
<213> ORGANISM: Artificial Sequence
<220> FEATURE:
<223> OTHER INFORMATION: Completely Synthesized

<400> SEQUENCE: 75

Ile Leu His Gln Pro Lys Lys Ser Met Asn Ser Val Thr Arg
1               5                   10

<210> SEQ ID NO 76
<211> LENGTH: 6
<212> TYPE: PRT
<213> ORGANISM: Artificial Sequence
<220> FEATURE:
<223> OTHER INFORMATION: Completely Synthesized

<400> SEQUENCE: 76

Thr Pro Val Asp Thr Lys
1               5
```

-continued

```
<210> SEQ ID NO 77
<211> LENGTH: 7
<212> TYPE: PRT
<213> ORGANISM: Artificial Sequence
<220> FEATURE:
<223> OTHER INFORMATION: Completely Synthesized

<400> SEQUENCE: 77

Asp Lys Leu Pro Leu Glu Lys
1               5

<210> SEQ ID NO 78
<211> LENGTH: 8
<212> TYPE: PRT
<213> ORGANISM: Artificial Sequence
<220> FEATURE:
<223> OTHER INFORMATION: Completely Synthesized

<400> SEQUENCE: 78

Gln Gly Gln Pro Val Val Pro Pro
1               5

<210> SEQ ID NO 79
<211> LENGTH: 22
<212> TYPE: PRT
<213> ORGANISM: Artificial Sequence
<220> FEATURE:
<223> OTHER INFORMATION: Completely Synthesized

<400> SEQUENCE: 79

Ser Ser Arg Cys Thr Pro Pro Ala Asp Ser Glu Leu Val Ser Phe
1               5                   10                  15

Cys Tyr Leu His Met Arg
            20

<210> SEQ ID NO 80
<211> LENGTH: 9
<212> TYPE: PRT
<213> ORGANISM: Artificial Sequence
<220> FEATURE:
<223> OTHER INFORMATION: Completely Synthesized

<400> SEQUENCE: 80

Arg Lys Gly Asp Ala Ala Cys Ser Arg
1               5

<210> SEQ ID NO 81
<211> LENGTH: 22
<212> TYPE: PRT
<213> ORGANISM: Artificial Sequence
<220> FEATURE:
<223> OTHER INFORMATION: Completely Synthesized

<400> SEQUENCE: 81

Leu Val Tyr Asp Met Val Val Ser Thr Asp Ser Ser Gly Leu Pro Lys
1               5                   10                  15

Ala Ala Ser Leu Leu Pro
            20

<210> SEQ ID NO 82
<211> LENGTH: 20
<212> TYPE: PRT
<213> ORGANISM: Artificial Sequence
<220> FEATURE:
<223> OTHER INFORMATION: Completely Synthesized

<400> SEQUENCE: 82
```

```
Gly Glu Glu Thr Glu Asn Lys Lys Ile Gly Cys Thr Val Asn Leu Met
1               5                   10                  15

Asn Phe Tyr Lys
            20

<210> SEQ ID NO 83
<211> LENGTH: 7
<212> TYPE: PRT
<213> ORGANISM: Artificial Sequence
<220> FEATURE:
<223> OTHER INFORMATION: Completely Synthesized

<400> SEQUENCE: 83

Leu Ala Glu Val Ile Leu Lys
1               5

<210> SEQ ID NO 84
<211> LENGTH: 7
<212> TYPE: PRT
<213> ORGANISM: Artificial Sequence
<220> FEATURE:
<223> OTHER INFORMATION: Completely Synthesized

<400> SEQUENCE: 84

Leu Ala Glu Val Ile Leu Lys
1               5

<210> SEQ ID NO 85
<211> LENGTH: 11
<212> TYPE: PRT
<213> ORGANISM: Artificial Sequence
<220> FEATURE:
<223> OTHER INFORMATION: Completely Synthesized

<400> SEQUENCE: 85

Thr Cys Ala Arg Asp Ser Gly Tyr Asp Ser Leu
1               5                   10

<210> SEQ ID NO 86
<211> LENGTH: 15
<212> TYPE: PRT
<213> ORGANISM: Artificial Sequence
<220> FEATURE:
<223> OTHER INFORMATION: Completely Synthesized

<400> SEQUENCE: 86

Pro Pro Glu Thr Ser Ser Lys Gly Ser Asp Ser Glu Leu Lys Lys
1               5                   10                  15

<210> SEQ ID NO 87
<211> LENGTH: 7
<212> TYPE: PRT
<213> ORGANISM: Artificial Sequence
<220> FEATURE:
<223> OTHER INFORMATION: Completely Synthesized

<400> SEQUENCE: 87

Pro Ala Thr Val Gln Ser Arg
1               5

<210> SEQ ID NO 88
<211> LENGTH: 7
<212> TYPE: PRT
<213> ORGANISM: Artificial Sequence
<220> FEATURE:
<223> OTHER INFORMATION: Completely Synthesized
```

```
<400> SEQUENCE: 88

Glu Leu Thr Glu Phe Ala Lys
1               5

<210> SEQ ID NO 89
<211> LENGTH: 7
<212> TYPE: PRT
<213> ORGANISM: Artificial Sequence
<220> FEATURE:
<223> OTHER INFORMATION: Completely Synthesized

<400> SEQUENCE: 89

Leu Val Ile Thr Thr Asp Arg
1               5

<210> SEQ ID NO 90
<211> LENGTH: 21
<212> TYPE: PRT
<213> ORGANISM: Artificial Sequence
<220> FEATURE:
<223> OTHER INFORMATION: Completely Synthesized

<400> SEQUENCE: 90

Ser Thr Ser Pro Gly Lys Tyr Pro His Pro Gly Leu Ala Asp Phe Ala
1               5                   10                  15

Asp Asn Leu Ile Lys
            20

<210> SEQ ID NO 91
<211> LENGTH: 7
<212> TYPE: PRT
<213> ORGANISM: Artificial Sequence
<220> FEATURE:
<223> OTHER INFORMATION: Completely Synthesized

<400> SEQUENCE: 91

His Arg Glu Ala Ala Gly Asn
1               5

<210> SEQ ID NO 92
<211> LENGTH: 9
<212> TYPE: PRT
<213> ORGANISM: Artificial Sequence
<220> FEATURE:
<223> OTHER INFORMATION: Completely Synthesized

<400> SEQUENCE: 92

Thr Asp Phe Val Gln Met Ala Val Leu
1               5

<210> SEQ ID NO 93
<211> LENGTH: 14
<212> TYPE: PRT
<213> ORGANISM: Artificial Sequence
<220> FEATURE:
<223> OTHER INFORMATION: Completely Synthesized

<400> SEQUENCE: 93

Glu Ile Pro Ala Val Pro Ile Leu His Ser Met Val Gln Lys
1               5                   10

<210> SEQ ID NO 94
<211> LENGTH: 37
<212> TYPE: PRT
<213> ORGANISM: Artificial Sequence
```

```
<220> FEATURE:
<223> OTHER INFORMATION: Completely Synthesized

<400> SEQUENCE: 94

Leu Leu Gln Glu Arg Val Thr Lys Asp His Val Phe Trp Ser Val Ser
1               5                   10                  15

Gly Val Asp Ala Asp Pro Asp Leu Val His Val Glu Ala Gln Asp Leu
            20                  25                  30

Gly Gly Asp Phe Arg
        35

<210> SEQ ID NO 95
<211> LENGTH: 12
<212> TYPE: PRT
<213> ORGANISM: Artificial Sequence
<220> FEATURE:
<223> OTHER INFORMATION: Completely Synthesized

<400> SEQUENCE: 95

Arg Tyr Pro Ala Ala Gly Ile Gly Phe Val Phe Leu
1               5                   10

<210> SEQ ID NO 96
<211> LENGTH: 13
<212> TYPE: PRT
<213> ORGANISM: Artificial Sequence
<220> FEATURE:
<223> OTHER INFORMATION: Completely Synthesized

<400> SEQUENCE: 96

Asp Val Ser Gln Glu Leu Asp Pro Asp Leu Tyr Lys Gln
1               5                   10

<210> SEQ ID NO 97
<211> LENGTH: 16
<212> TYPE: PRT
<213> ORGANISM: Artificial Sequence
<220> FEATURE:
<223> OTHER INFORMATION: Completely Synthesized

<400> SEQUENCE: 97

Tyr Glu Asn Lys Gly Leu Met Ile Ile Asp Glu Glu Glu Phe Leu Leu
1               5                   10                  15

<210> SEQ ID NO 98
<211> LENGTH: 15
<212> TYPE: PRT
<213> ORGANISM: Artificial Sequence
<220> FEATURE:
<223> OTHER INFORMATION: Completely Synthesized

<400> SEQUENCE: 98

Ile Tyr Ala Cys Ala Leu Asp Gln Thr Gly Leu Leu Glu Met Lys
1               5                   10                  15

<210> SEQ ID NO 99
<211> LENGTH: 9
<212> TYPE: PRT
<213> ORGANISM: Artificial Sequence
<220> FEATURE:
<223> OTHER INFORMATION: Completely Synthesized

<400> SEQUENCE: 99

Val Ile Thr Ser Asn Thr Ile Val Arg
1               5
```

<210> SEQ ID NO 100
<211> LENGTH: 23
<212> TYPE: PRT
<213> ORGANISM: Artificial Sequence
<220> FEATURE:
<223> OTHER INFORMATION: Completely Synthesized

<400> SEQUENCE: 100

Asp Met Asp Ile Ile Thr Lys Phe Leu Lys Phe Leu Leu Gly Val Trp
1               5                   10                  15

Ala Lys Glu Leu Asn Ala Arg
            20

<210> SEQ ID NO 101
<211> LENGTH: 19
<212> TYPE: PRT
<213> ORGANISM: Artificial Sequence
<220> FEATURE:
<223> OTHER INFORMATION: Completely Synthesized

<400> SEQUENCE: 101

Lys Leu Phe Asp Ser Thr Ile Ala Asp Glu Gly Thr Trp Thr Leu Glu
1               5                   10                  15

Asp Arg Lys

<210> SEQ ID NO 102
<211> LENGTH: 8
<212> TYPE: PRT
<213> ORGANISM: Artificial Sequence
<220> FEATURE:
<223> OTHER INFORMATION: Completely Sythesized

<400> SEQUENCE: 102

Cys Leu His Met Phe Leu Gln Glu
1               5

<210> SEQ ID NO 103
<211> LENGTH: 20
<212> TYPE: PRT
<213> ORGANISM: Artificial Sequence
<220> FEATURE:
<223> OTHER INFORMATION: Completely Synthesized

<400> SEQUENCE: 103

Pro Glu Leu Gln Arg Leu Ile Ser Gly Asp Asn Ala Glu Ile Asp Leu
1               5                   10                  15

Glu Asp Leu Lys
            20

<210> SEQ ID NO 104
<211> LENGTH: 15
<212> TYPE: PRT
<213> ORGANISM: Artificial Sequence
<220> FEATURE:
<223> OTHER INFORMATION: Completely Synthesized

<400> SEQUENCE: 104

Met Glu Val Ala Glu Leu Gly Phe Pro Glu Thr Ala Val Ser Gln
1               5                   10                  15

<210> SEQ ID NO 105
<211> LENGTH: 20
<212> TYPE: PRT
<213> ORGANISM: Artificial Sequence
<220> FEATURE:

```
<223> OTHER INFORMATION: Completely Synthesized

<400> SEQUENCE: 105

Met Asp His Tyr Val Ala Thr Thr Glu Phe Leu Trp Ser Val Pro Cys
1               5                   10                  15

Ser Pro Gln Ser
            20

<210> SEQ ID NO 106
<211> LENGTH: 7
<212> TYPE: PRT
<213> ORGANISM: Artificial Sequence
<220> FEATURE:
<223> OTHER INFORMATION: Completely Synthesized

<400> SEQUENCE: 106

Arg Leu Thr Asn Leu Ser Ser
1               5

<210> SEQ ID NO 107
<211> LENGTH: 24
<212> TYPE: PRT
<213> ORGANISM: Artificial Sequence
<220> FEATURE:
<223> OTHER INFORMATION: Completely Synthesized

<400> SEQUENCE: 107

Ser Asp Thr Thr Ile Lys Pro Asn Pro Glu Asn Thr Gly Pro Thr Leu
1               5                   10                  15

Glu Trp Asp Asn Tyr Asp Leu Arg
            20

<210> SEQ ID NO 108
<211> LENGTH: 7
<212> TYPE: PRT
<213> ORGANISM: Artificial Sequence
<220> FEATURE:
<223> OTHER INFORMATION: Completely Synthesized

<400> SEQUENCE: 108

Gln Tyr Val Val Gln Leu Lys
1               5

<210> SEQ ID NO 109
<211> LENGTH: 7
<212> TYPE: PRT
<213> ORGANISM: Artificial Sequence
<220> FEATURE:
<223> OTHER INFORMATION: Completely Synthesized

<400> SEQUENCE: 109

Glu Phe Val Glu Val Ile Lys
1               5

<210> SEQ ID NO 110
<211> LENGTH: 11
<212> TYPE: PRT
<213> ORGANISM: Artificial Sequence
<220> FEATURE:
<223> OTHER INFORMATION: Completely Synthesized

<400> SEQUENCE: 110

Ile Glu Glu Glu Thr Ser Gly Asp Leu Gln Lys
1               5                   10
```

<210> SEQ ID NO 111
<211> LENGTH: 19
<212> TYPE: PRT
<213> ORGANISM: Artificial Sequence
<220> FEATURE:
<223> OTHER INFORMATION: Completely Synthesized

<400> SEQUENCE: 111

Met Tyr Glu Arg Tyr Ser Leu Ser Phe Met Asp Leu Gln Ile Met Val
1               5                   10                  15

Gly Arg Val

<210> SEQ ID NO 112
<211> LENGTH: 15
<212> TYPE: PRT
<213> ORGANISM: Artificial Sequence
<220> FEATURE:
<223> OTHER INFORMATION: Completely Synthesized

<400> SEQUENCE: 112

Val Arg Thr Lys His Thr Ser Gly Leu Ser Tyr Gly Gln Glu Ser
1               5                   10                  15

<210> SEQ ID NO 113
<211> LENGTH: 26
<212> TYPE: PRT
<213> ORGANISM: Artificial Sequence
<220> FEATURE:
<223> OTHER INFORMATION: Completely Synthesized

<400> SEQUENCE: 113

Gly Gly Ala Gln Val Gln Gln Val Leu Asn Ile Glu Cys Leu Arg Asp
1               5                   10                  15

Phe Leu Thr Pro Pro Leu Leu Ser Val Arg
            20                  25

<210> SEQ ID NO 114
<211> LENGTH: 22
<212> TYPE: PRT
<213> ORGANISM: Artificial Sequence
<220> FEATURE:
<223> OTHER INFORMATION: Completely Synthesized

<400> SEQUENCE: 114

Ala Gly Ala Glu Ala Ala Lys Asn Ala Leu Asn Gly Ile Arg Phe Asp
1               5                   10                  15

Pro Glu Asn Pro Gln Thr
            20

<210> SEQ ID NO 115
<211> LENGTH: 26
<212> TYPE: PRT
<213> ORGANISM: Artificial Sequence
<220> FEATURE:
<223> OTHER INFORMATION: Completely Synthesized

<400> SEQUENCE: 115

Glu Ser Thr Ala Val Ala Leu Ser Leu Ile Asn Leu Leu Gly Ile Leu
1               5                   10                  15

Pro Ile Gln Asn Thr Ser Thr Ser Leu His
            20                  25

<210> SEQ ID NO 116
<211> LENGTH: 7
<212> TYPE: PRT

```
<213> ORGANISM: Artificial Sequence
<220> FEATURE:
<223> OTHER INFORMATION: Completely Synthesized

<400> SEQUENCE: 116

Met Ala His Gly Asp Leu Lys
1               5

<210> SEQ ID NO 117
<211> LENGTH: 20
<212> TYPE: PRT
<213> ORGANISM: Artificial Sequence
<220> FEATURE:
<223> OTHER INFORMATION: Completely Synthesized

<400> SEQUENCE: 117

Met Ser Arg Ile Glu Lys Met Ser Ile Leu Gly Val Arg Ser Phe Gly
1               5                   10                  15

Ile Glu Asp Lys
            20

<210> SEQ ID NO 118
<211> LENGTH: 15
<212> TYPE: PRT
<213> ORGANISM: Artificial Sequence
<220> FEATURE:
<223> OTHER INFORMATION: Completely Synthesized

<400> SEQUENCE: 118

Thr Glu Phe Leu Gln Arg Glu Ser Glu Arg Leu Glu Leu Met Asn
1               5                   10                  15

<210> SEQ ID NO 119
<211> LENGTH: 18
<212> TYPE: PRT
<213> ORGANISM: Artificial Sequence
<220> FEATURE:
<223> OTHER INFORMATION: Completely Synthesized

<400> SEQUENCE: 119

Val Lys Glu Leu Asn His Tyr Leu Glu Ala Glu Lys Ser Cys Arg Thr
1               5                   10                  15

Asp Leu

<210> SEQ ID NO 120
<211> LENGTH: 29
<212> TYPE: PRT
<213> ORGANISM: Artificial Sequence
<220> FEATURE:
<223> OTHER INFORMATION: Completely Synthesized

<400> SEQUENCE: 120

Glu Pro Ala Leu Asp Gly Gly Phe Gln Met His Tyr Glu Lys Thr Pro
1               5                   10                  15

Phe Asp Gln Leu Ala Phe Ile Glu Glu Leu Phe Ser Leu
            20                  25

<210> SEQ ID NO 121
<211> LENGTH: 7
<212> TYPE: PRT
<213> ORGANISM: Artificial Sequence
<220> FEATURE:
<223> OTHER INFORMATION: Completely Synthesized

<400> SEQUENCE: 121
```

```
Ser Asp Ala Glu His Phe Lys
1               5

<210> SEQ ID NO 122
<211> LENGTH: 8
<212> TYPE: PRT
<213> ORGANISM: Artificial Sequence
<220> FEATURE:
<223> OTHER INFORMATION: Completely Synthesized

<400> SEQUENCE: 122

Leu Leu Thr Glu Met Val Asn Arg
1               5

<210> SEQ ID NO 123
<211> LENGTH: 14
<212> TYPE: PRT
<213> ORGANISM: Artificial Sequence
<220> FEATURE:
<223> OTHER INFORMATION: Completely Synthesized

<400> SEQUENCE: 123

Ser Leu Ser Lys Asn Leu Ser Leu Asn Ser Gln Ala Leu Lys
1               5                   10

<210> SEQ ID NO 124
<211> LENGTH: 16
<212> TYPE: PRT
<213> ORGANISM: Artificial Sequence
<220> FEATURE:
<223> OTHER INFORMATION: Completely Synthesized

<400> SEQUENCE: 124

Cys Ile Lys Leu Lys Ile Asp Ser Glu Ile Lys Lys Thr Val Val Leu
1               5                   10                  15

<210> SEQ ID NO 125
<211> LENGTH: 14
<212> TYPE: PRT
<213> ORGANISM: Artificial Sequence
<220> FEATURE:
<223> OTHER INFORMATION: Completely Synthesized

<400> SEQUENCE: 125

Asp Gly Asp Ser Glu Gly Thr Pro Val Asn Lys Leu Leu Lys
1               5                   10

<210> SEQ ID NO 126
<211> LENGTH: 16
<212> TYPE: PRT
<213> ORGANISM: Artificial Sequence
<220> FEATURE:
<223> OTHER INFORMATION: Completely Synthesized

<400> SEQUENCE: 126

Cys Ser Ile Gly Val Val Asp Gln Gly Cys Phe Pro Lys Pro Leu Leu
1               5                   10                  15

<210> SEQ ID NO 127
<211> LENGTH: 16
<212> TYPE: PRT
<213> ORGANISM: Artificial Sequence
<220> FEATURE:
<223> OTHER INFORMATION: Completely Synthesized
```

```
<400> SEQUENCE: 127

Gly Val Arg Ile Tyr Asp Gly Glu Glu Lys Ile Lys Phe Asp Ala Gly
1               5                   10                  15
```

SERUM MARKERS ASSOCIATED WITH EARLY AND OTHER STAGES OF BREAST CANCER

CROSS REFERENCE TO RELATED APPLICATIONS

This application is the U.S. national stage of International Application No. PCT/US2010/041813, filed Jul. 13, 2010, claiming priority to U.S. application Ser. No. 12/670,343, file Jan. 22, 2010, now U.S. Pat. No. 8,333,880, which is the U.S. national stage of International Application No. PCT/US2008/000509, filed Jan. 15, 2008, claiming priority to U.S. Provisional Application No. 60/962,081, filed Jul. 26, 2007, and to U.S. Provisional Application No. 61/225,254, filed Jul. 14, 2009, and is a continuation-in-part application of U.S. application Ser. No. 12/670,343, filed Jan. 22, 2010, now U.S. Pat. No. 8,333,880, the contents of all of which are incorporated by reference herein, in their entireties and for all purposes.

FIELD OF THE INVENTION

This invention relates generally to the identification of new disease-specific markers, in particular the identification of markers specific for a given cancer or cancer stage, and the use of such markers to determine a diagnosis, prognosis or therapeutic treatment for a subject. More specifically, the invention relates to detection and identification of low copy number cancer polypeptides comprising cancer peptide motifs, especially polypeptides comprising markers of particular stages of breast cancer, and to diagnosing or differentiating among different stages of breast cancer.

BACKGROUND OF THE INVENTION

Blood is a rich and readily accessible source for the detection of diagnostic markers and therapeutic targets in many human diseases. Currently, however, only a handful of plasma proteins are routinely used in the clinic for diagnostic purposes. It is generally established that these low-abundance proteins contain most of the useful biomarkers, including those that are produced by specific diseases such as cardiovascular diseases, neurological disorders, autoimmune diseases, and cancer, but these low abundance proteins are difficult to detect because they are often masked by high-abundance proteins, particularly serum albumin. In serum and plasma, the quantities of high-abundance proteins and some low-abundance proteins span over 10 orders of magnitude. For example, low-abundance proteins such as growth factors and cytokines are present in one millionth to one trillionth of the abundant proteins.

Serum albumin, the most abundant protein in serum typically present at 45-50 mg/ml, constitutes about 55% of total serum protein. Albumin functions as a scaffold for binding proteins, lipids, small molecules in the intracellular space and has been found to form associations with peptide hormones such as insulin and glucagon; serum amyloid A, interferons, bradykinin, the amino-terminal peptide of HIV-1, gp41, the 14-kDa fragment of streptococcal protein G, and others. In order to carry out such diverse functions, it is likely that serum albumin population is heterogeneous and contains many different albumin complexes. Technologies currently available such as two-dimensional polyacrylamide gel electrophoresis (2-D PAGE) developed by O'Farrel (O'Farrel, P., (1975) J. Biol. Chem. 250: 4007-4021) do not allow separation of protein complexes because they were carried out under denaturing conditions which dissociated the serum albumin complexes.

Due to the wide range of protein concentrations and high structural complexity of the constituent proteins, analysis of the proteome of plasma and serum represents a challenge. At present, low-abundance proteins can only be detected for further analysis by removal of abundant proteins to decrease both dynamic concentration range and complexity.

One approach for removing the most abundant plasma proteins, yielding an enriched pool of low-abundance proteins, is immunoaffinity chromatography (Gallent, S R., (2008) Methods Mol. Biol. 421:53-60). Although this method has increased the number of detectable proteins in plasma/serum analysis, it has several major drawbacks. First, up to 90% of potential protein biomarkers are known to be associated with the highly abundant carrier proteins in blood such as serum albumin. Depletion of the high-abundance proteins often removes many potentially important marker proteins. In addition, some low-abundance proteins may be retained in the column through nonspecific binding, resulting in their loss from the flow-through fractions. Extensive sample handling also increases the chance of sample loss and protein degradation, resulting in substantial sample-to-sample variation. The depletion process is also time-consuming and the immunoaffinity columns are rather expensive.

Realizing that most of potential protein biomarkers are likely to be associated with the highly abundant carrier proteins in blood such as serum albumin, a different approach for partial enrichment of the low-abundance proteins is to capture serum albumin onto a solid support followed by selectively eluting the low-abundance proteins with solvents. However, serum albumin is composed of mixtures of complexes and selective removal of bound proteins based on affinity without first resolving the albumin complexes will have difficulty in obtaining the low-abundance proteins. Most of proteins detected by this procedure were abundant proteins present naturally and not related to the specific disease.

Diseases such as cancer are caused by, for example, DNA damage (i.e., mutation) in genes that regulate cell growth and division. It is often characterized by the production of abnormal proteins. Because of the difficulties indicated above it is virtually impossible to isolate the low-abundance disease proteins. Compounding the problem for their detection is the fact that in many diseased cells, these disease-associated proteins are degraded by proteolytic enzymes, generating peptide fragments that are subsequently released into the bloodstream. Being low molecular weight in nature, these peptide fragments generally have a half-life of only several hours and most of them are cleared from circulation by the kidney (Lowenthal et al. (2005) Clinical Chemistry 51: 1933-45). However, some of these peptide fragments have high affinity for serum albumin which has a rather long half-life of about 19 days. By their association with serum albumin to form complexes the longevity of these disease-related peptide fragments can be increased by approximately 60 to 100-fold (Dennis et al. (2002) J. Biol. Chem. 277: 35035-43).

Breast cancer is the second most common cause of cancer death in women in the United States and is also a cause of disability, psychological trauma, and economic loss. Breast cancer morbidity increases significantly if it is not detected early in its progression. Early detection of breast cancer before symptoms appear is highly desirable. Even so, it is estimated that between 15 to 25% of women with early stage breast cancer are currently missed by mammography particularly if they have dense breasts. The challenge is to address the inherent limitations of mammography by developing a simple

SUMMARY OF THE INVENTION

The invention provides a method of identifying a disease-specific marker, comprising the following steps. A biological sample comprising a plurality of serum albumin complexes is obtained from a reference subject, and the serum albumin complexes are separated by a two-dimensional electrophoresis directly on a protein blotting membrane (i.e., two-dimensional membrane electrophoresis) to generate a reference separation profile, A biological sample comprising a plurality of serum albumin complexes from a diseased subject, and the serum albumin complexes are separated by a two-dimensional membrane electrophoresis to generate a disease separation profile. The reference separation profile is compared with the disease separation profile to determine the difference in the number, distribution or both number and distribution of the separated serum albumin complexes between the reference and disease separation profiles. The difference represents a disease-specific marker.

The invention also provides a method of diagnosing a disease in a test subject, comprising the following steps. A biological sample comprising a plurality of serum albumin complexes is obtained from a test subject, and the serum albumin complexes are separated by a two-dimensional membrane electrophoresis to generate a test separation profile. A reference separation profile is provided, and the test separation profile is compared with the reference separation profile. A substantial similarity between the test separation profile and the reference profile indicates that the test subject has the disease represented by the reference separation profile. The method further comprises treating the test subject having the disease with a therapy suitable for treating the disease.

The invention further provides a method of staging cancer in a test subject, comprising the following steps. A biological sample comprising a plurality of serum albumin complexes from a test subject, and the serum albumin complexes are separated by a two-dimensional membrane electrophoresis to generate a test separation profile. A plurality of stage-specific reference separation profiles are provided, and the test separation profile is compared with the stage-specific reference separation profiles. A substantial similarity between the test separation profile and a stage-specific reference profile indicates that the test subject has the specific stage of cancer represented by the stage-specific separation profile. For example, for breast cancer, the stage-specific reference separation profiles may comprise first, second, third and fourth stage-specific reference separation profiles representing stages I, II, III and IV of breast cancer, respectively. The method may further comprise treating the test subject having the specific stage of cancer with a therapy suitable for treating the specific stage of cancer.

The comparing step of the above methods may be performed on a computer. The computer may generate a report, for example, on screen or paper.

A biological sample may comprise a biological fluid. The biological sample may also comprise a hydrophobic or hydrophilic fraction of the biological fluid. The biological fluid may be selected from the group consisting of blood, serum, saliva, urine, lymph, perspiration, mucus, cerebrospinal fluid, lachrymal fluid, vitreous humor, semen, vaginal secretions, and mammary gland secretions, preferably blood and serum.

A reference separation profile may be a separation profile of a healthy subject or a subject having a specific stage of a disease. For example, a reference separation profile may represent an early stage of breast cancer (e.g., Stage 0, I or II breast cancer).

The disease may be cancer, a neurological disease, autoimmune disease, or a heart disease. The cancer may be selected from the group consisting of adenocarcinoma of rectum, bladder cancer, breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, and stomach adenocarcinoma, preferably breast cancer and glioma. The neurological disease may be Alzheimer's disease, multiple sclerosis, Parkinson's disease, or migraine headaches.

The invention provides a method for detecting a low copy number polypeptide in a biological sample. In general, the methods comprise obtaining a biological sample comprising a plurality of serum albumin complexes, optionally separating the biological sample into hydrophilic and hydrophobic fractions, separating the serum albumin complexes by a two-dimensional membrane electrophoresis, digesting at least one separated serum albumin complex on the membrane with a protease, and detecting the polypeptide in the digested complex. The polypeptide may comprise a cancer peptide motif. In some aspects, the method may further comprise determining the amino acid sequence of the detected polypeptide or cancer peptide motif. Also provided is a kit for detecting a low copy number polypeptide in a biological sample. The kit may comprise one or more membranes suitable for a two-dimensional membrane electrophoresis, a protease, and instructions for using the kit in this method.

The invention features an isolated serum albumin complex. The complex may comprise a breast cancer complex selected from the group consisting of Stage 0 Complexes, Stage I Complexes, Stage II Complexes, Stage III Complexes and Stage IV Complexes. The Stage 0 Complexes comprise Stage 0 Complex 1, Stage 0 Complex 2, Stage 0 Complex 3 and Stage 0 Complex 4. The Stage I Complexes comprise Stage I Complex 1, Stage I Complex 2, Stage I Complex 3, Stage I Complex 4, Stage I Complex 5, Stage I Complex 6, Stage I Complex 7 and Stage I Complex 8. The breast cancer complex may comprise a cancer polypeptide, which comprises a cancer peptide motif. The cancer polypeptide may correspond to a protein that is previously known to be associated with cancer. The cancer polypeptide may be foreign to the immune system of a host, and cause an autoimmune disease in the host. Also featured are the cancer peptide motif, the cancer polypeptide, and the corresponding cancer protein, each of which may be isolated. A cancer peptide motif may have an amino acid sequence selected from SEQ ID NOs: 1-122.

The invention further features a method of producing antibodies, comprising administering an effective amount of a cancer polypeptide of the invention to an immunologically competent host, and recovering antibodies from the host. The cancer polypeptide may comprise a cancer peptide motif having an amino acid sequence selected from SEQ ID NOs: 1-122. The polypeptide has at least about 6, 10, 14, 20, 25 or 30 amino acids. Preferably, the polypeptide has about 14-20 amino acids. Antibodies obtained by this method include antibodies that bind specifically to a cancer polypeptide comprising a cancer peptide motif having an amino acid sequence selected from SEQ ID NOs: 1-122, or to polypeptide with SEQ ID NOs: 44 and 123-127, more preferably SEQ ID NOs: 44, 125 and 127.

BRIEF DESCRIPTION OF THE DRAWINGS

FIGS. 1A and 1B show one-dimensional separation profiles of proteins at pH 5.0 (A) and pH 8.0 (B). Arrows indicate where the protein or mixture was spotted. Lane 1: a mixture of all proteins; lane 2: cytochrome c; lane 3: lentil lectin; lane 4: myoglobin; lane 5: β-lactoglobulin A; lane 6: glucose oxidase; and lane 7: amylogluocosidase.

DETAILED DESCRIPTION OF THE INVENTION

Figure 2A:
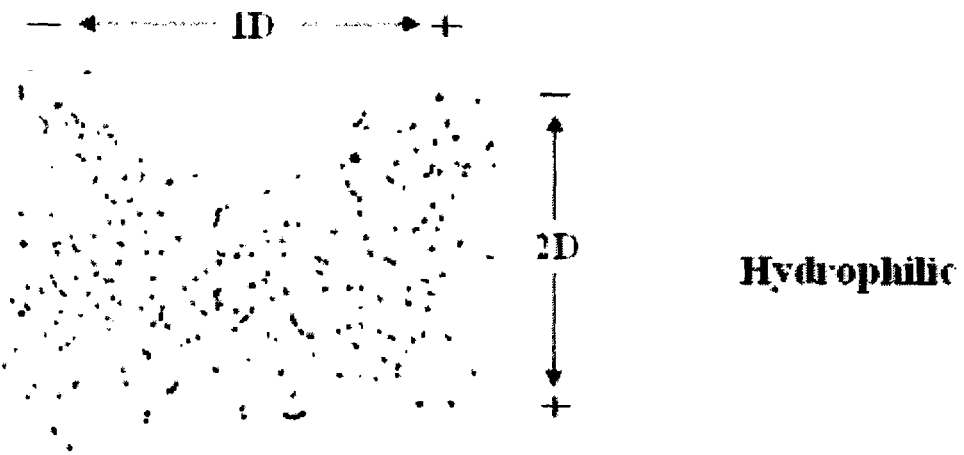
FIGS. 2A and 2B show separation profiles of serum albumin complexes in the hydrophilic fraction (A) and the hydrophobic fraction (B) of a serum sample from a healthy individual.

The invention provides a method of identifying a disease-specific marker, comprising the following steps. A biological sample comprising a plurality of serum albumin complexes is obtained from a reference subject, and the serum albumin complexes are separated by a two-dimensional electrophoresis directly on a protein blotting membrane (i.e., two-dimensional membrane electrophoresis) to generate a reference separation profile. A biological sample comprising a plurality of serum albumin complexes is obtained from a diseased subject, and the serum albumin complexes are separated by a two-dimensional membrane electrophoresis to generate a disease separation profile. The reference separation profile is compared with the disease separation profile to determine the difference in the number, distribution or both number and distribution of the separated serum albumin complexes between the reference and disease separation profiles. The difference represents a disease-specific marker.

The invention also provides a method of diagnosing a disease in a test subject, comprising the following steps. A biological sample comprising a plurality of serum albumin complexes is obtained from a test subject, and the serum albumin complexes are separated by a two-dimensional membrane electrophoresis to generate a test separation profile. A reference separation profile is provided, and the test separation profile is compared with the reference separation profile. A substantial similarity between the test separation profile and the reference profile indicates that the test subject has the disease represented by the reference separation profile. The method further comprises treating the test subject having the disease with a therapy suitable for treating the disease.

A "subject" means a animal, preferably a mammal such as a human and non-human primate, as well as a companion, farm, or experimental animal such as a rabbit, dog, cat, rat, mouse, horse, cow, pig, and the like, most preferably a human. A "reference subject" means a subject who is known to be healthy or have a disease. A "diseased subject" is a subject known to have a disease. A diseased subject may have the same disease as a reference subject, but at a different stage. A "test subject" means a subject whose condition with respect to a disease is unknown and to be determined.

The term "a plurality of" means two, three, four, five or more.

A "biological sample" may be obtained from any type of biological material including cells, tissues, fluids, and the like from a subject. Non-limiting examples of fluids include blood, cerebro-spinal fluid, feces, gingival crevicular fluid, lachrymal fluid, lymph, perspiration, mammary gland secretions, mucus, saliva, semen, serum, sputum, synovial fluid, tears, urine, vaginal secretions, and vitreous humor, preferably blood and serum. The biological sample can be separated into hydrophobic and hydrophilic fractions.

Albumin complexes can be separated on a membrane by any means suitable in the art, including polyacrylamide gel electrophoresis followed by transfer to the membrane. Preferably, the separation is carried out directly on the blot membrane using membrane electrophoresis. The membrane electrophoresis is preferably two-dimensional membrane electrophoresis as described and exemplified herein. Any membrane suitable for separating serum albumin complexes can be used.

Membranes for use in the present invention can be either hydrophobic or hydrophilic, and preferably have a low charge or a net neutral charge. For purposes of the present invention, it is understood that polymeric membranes designated as "neutral" are generally not devoid of charge, but either have a net neutral charge or a slight positive or negative charge. Hydrophobic membranes suitable for use in the present invention include membranes comprising fluorinated polymers such as polyvinylidene difluoride (PVDF, also known in the art as polyvinylidene fluoride), polytetrafluoroethylene (PTFE), and the like; polyolefins such as polyethylene, polypropylene, polymethylpentene and the like; polystyrene or substituted polystyrenes; polysulfones such as polyethersulfone and the like; polyesters such as polyethylene terephthalate; polybutylene terephthalate and the like; polyacrylates and polycarbonates; polyurethane and vinyl polymers such as polyvinyl chloride and polyacrylonitriles; and mixtures of the above-listed polymers. Additionally, the hydrophobic membranes can comprise copolymers; e.g., of butadiene and styrene; fluorinated ethylene-propylene copolymer; and the like. Preferably, the hydrophobic membranes comprise polymeric fluorocarbons such as polyvinylidene difluoride (PVDF).

The hydrophobic membranes can also comprise modified forms of the above polymers, such as are known in the art. For example, hydrophobic polymeric membranes can be modified to contain fixed formal positive charge groups by contacting the membranes with a polyamine or a polyamido-polyamine epichlorohydrin resin.

Hydrophilic membranes suitable for use in the present invention include membranes comprising polyamides such as nylons (e.g., nylon 66, nylon 6, nylon 610 or nylon 46); polyimides; polyesters; polyvinyl alcohols; polyvinylamines; polybenzylamides; polyvinylimidazolines; polydiallylamines; and mixtures thereof. Preferred hydrophilic membranes comprise neutral or slightly positively charged nylon polymers (e.g., Hybond™-N or Hybond™-NX blotting membranes, available from Amersham Biosciences, Piscataway, N.J.).

A disease may be cancer, a neurological disease, an autoimmune disease, or a heart disease. The cancer may be adenocarcinoma of rectum, bladder cancer, breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, prostate cancer, pancreatic cancer, renal cell carcinoma, small bowel malignant stromal tumor, or stomach adenocarcinoma, preferably breast cancer and glioma. The neurological disease may be Alzheimer's disease, multiple sclerosis, Parkinson's disease, or migraine headaches. Preferably, the cancer is breast cancer.

A disease may be caused by DNA damage (i.e., mutation) in genes that regulate cell growth and division. Cancer may cause the body to produce abnormal proteins, and some of these proteins and fragments thereof bind to serum albumin complexes, resulting in new and different serum albumin complexes. The association of new peptide fragments comprising cancer peptide motifs to existing serum albumin complexes modifies the migration profile of the complexes in membrane electrophoresis. Accordingly, a two-dimensional membrane electrophoresis can be used to characterize the serum albumin separation profiles.

A "reference separation profile" refers to a separation profile of serum albumin complexes from a reference subject. Where the reference subject is a healthy individual, the reference separation profile shows a normal separation pattern of the serum albumin complexes and represents a healthy condition. Where the reference subject has a disease, the reference separation profile may show an abnormal separation pattern of the serum albumin complexes due to the disease, and represents the disease. Where the reference subject has a disease of a specific stage, the reference separation profile may show an abnormal separation pattern of the serum albumin complexes due to the specific stage of the disease, and represents the particular stage of the disease. Such a reference separation profile is stage-specific. A reference profile can also be a profile previously obtained from the same subject. Multiple reference separation profiles, including combinations of such profiles, may be used to increase the confidence in diagnosis.

A "disease separation profile" refers to a separation profile of serum albumin complexes from a diseased subject.

A "test separation profile" refers to a separation profile of serum albumin complexes from a test subject.

The invention further provides a method of staging cancer in a test subject, comprising the following steps. A biological sample comprising a plurality of serum albumin complexes from a test subject, and the serum albumin complexes are separated by a two-dimensional membrane electrophoresis to generate a test separation profile. A plurality of stage-specific reference separation profiles are provided, and the test separation profile is compared with the stage-specific reference separation profiles. A substantial similarity between the test separation profile and a stage-specific reference profile indicates that the test subject has the specific stage of cancer represented by the stage-specific separation profile. The method may further comprise treating the test subject having the specific stage of cancer with a therapy suitable for treating the specific stage of cancer.

The staging of cancer refers to the grouping of subjects according to the extent of their disease. Cancer stages are generally established according to the size of the tumor, whether the tumor has spread to the lymph nodes, and whether the cancer has metastasized. For example, breast cancer is generally classified into the following stages, defined by the National Cancer Institute: Stage 0, Stage I, Stage IIA, Stage IIB, Stage IIIA, Stage IIIB, Stage IIIC, and Stage IV. Stages 0-IIIA are considered early stage.

The invention features methods for diagnosing early stage breast cancer, particularly Stage 0, Stage I and Stage II breast cancer. In general, the methods comprise the steps of obtaining a biological sample comprising a plurality of serum albumin complexes from a test subject, separating the serum albumin complexes by a two-dimensional membrane electrophoresis to generate a test separation profile, and comparing the separation profile with one or more reference separation profiles, which are specific for Stage 0, Stage I or Stage II breast cancer. For example, the stage-specific reference separation profiles may comprise first, second, third and fourth stage-specific reference separation profiles representing stages I, II, III and IV of breast cancer, respectively. A substantial similarity between the test separation profile and one of the one or more stage-specific reference separation profiles indicates whether the subject has the stage of breast cancer represented by the stage-specific reference separation profile. Accordingly, a diagnosis can be made, and a suitable treatment can be adopted.

The number, distribution or both number and distribution of the separated serum albumin complexes are compared. A difference between a reference separation profile and a disease separation profile represents a marker specific for the disease. A serum albumin complex present only in a disease separation profile or a stage-specific separation profile is a disease-specific complex or stage-specific complex. Serum albumin complexes associated with early stage breast cancer have been identified as markers for early stage breast cancer, and characterized to determine their polypeptide contents.

A substantial similarity between a reference separation profile and a test separation profile indicates that the test subject has the disease represented by the reference separation profile. A test separation profile is "substantially similar" to a reference separation profile when both profiles exhibit the same separation pattern of serum albumin complexes (including the number, placement and/or relative intensity of protein spots), within the normal variations expected in 1) the intensity of protein spots, 2) the absolute distance of each spot from the origin along the length and/or width of the membrane, and 3) the relative distance of each spot from other spots on the membrane. One skilled in the art is familiar with, and can readily determine, the magnitude of these expected variations.

A "protein spot" on a membrane comprise a single protein, a protein complex, or a plurality of proteins. The spot can be visualized by any suitable visualization technique.

The comparing step in the methods of the invention may be performed on a computer. The computer may generate a report, for example, on screen or paper. The report may include a diagnosis for a test subject. It may also include recommendation of a therapy suitable for the diagnosed disease or the diagnosed stage of cancer.

In some aspects, the methods further comprise digesting one or more of the separated serum albumin complexes on the membrane with a protease, and then detecting and/or characterizing the digested polypeptides. Suitable proteases are known to those of ordinary skill in the art. Trypsin is preferred. Other enzymes such as Lys-C Endoproteinase, Asp-N Endoproteinase, Glu-C Endoproteinase, Chymotrypsin and V8 protease can also be used.

Digestion is carried out by excising the protein spot of interest from the membrane and destaining the protein. After excising, the protein can be reduced, for example, by using 20 mM (2-carboxyethyl)phosphine hydrochloride (TCEP) in 25 mM ammonium bicarbonate followed by alkylation with 40 mM iodoacetamide in 25 mM ammonium bicarbonate. Digestion can be carried out by an enzyme of interest. The supernatant can then be removed to a clean tube. The supernatants can be combined with an acid, and then subject to analysis.

Following digestion with a protease, the polypeptides in the serum albumin complex can be detected. Mass spectrometry is a preferred procedure to detect and characterize the polypeptides. The enzymatic digest can be used for mass spectrometric analysis using, for example, a capilliary HPLC with a 75 μm nanocolumn and a Thermo Fisher LTQ-Orbi-Trap XL, a hybrid system combining LTQ linear ion trap mass spectrometer with the Orbi mass analyzer. The resulting masses and spectra can be searched against a database using appropriate software.

Any suitable probes specific for detecting polypeptides of interest can be used, including antibodies that specifically bind to the polypeptides. Where probes are unavailable, or the polypeptide components of the complexes are unknown, it may be preferable to sequence the polypeptides. Any suitable sequencing methodology such as liquid chromatography with tandem spectrometry sequencing of individual peptides (LC/MS/MS) can be used. The sequences can be compared against reference sequences or any other database to determine if the polypeptides are associated with any particular stage of breast cancer. Newly discovered polypeptides (including protein fragments) can be added to an appropriate database.

One or more of the method steps may be embodied in computer-executable instructions stored on a computer readable storage medium. The computer readable storage medium may be essentially any tangible storage medium capable of storing instructions for performance by a general or specific purpose computer such as an optical disc, magnetic disk, or solid state device, for example. Generally, one or more of the steps can be performed on a computer specifically configured to carry out the one or more steps.

In some aspects, the methods further comprise treating the subject with a therapy suitable for treating a disease (e.g., breast cancer). The therapy can be specific for treating a particular stage of cancer (e.g., Stage 0, Stage I, Stage II, Stage III, or Stage IV of breast cancer). The therapy can comprise administering to the subject an effective amount of a therapeutic agent (e.g., pharmaceutical or biomolecule), radiation, and/or surgery. Therapeutic agents include biomolecules (e.g., antibodies) that have high affinity, for example, having $K_d$ of at least $10^{-4}$, $10^{-6}$, $10^{-8}$, $10^{-10}$, and $10^{-12}$ M, for newly identified cancer peptide motifs.

The methods can further be used to monitor the effectiveness of a disease treatment, for example, chemotherapy, radiation or any other treatment, by comparing separation profiles before and after treatment.

The invention features isolated serum albumin complexes, preferably disease-specific complexes (i.e., complexes present in a diseased subject, not a healthy subject) or stage-specific complexes (i.e., complexes present in a diseased subject at one stage, not another stage). In some preferred aspects, the serum albumin complexes comprise a breast cancer complex. A breast cancer complex is a serum albumin complex that is present in a breast cancer patient, but not in a healthy individual. It may be selected from the group consisting of complexes specific to Stage 0 (Stage 0 Complexes), Stage I (Stage I Complexes), Stage II (Stage II Complexes), Stage III (Stage III Complexes) and Stage IV (Stage IV Complexes). The Stage 0 Complexes comprise Stage 0 Complex 1, Stage 0 Complex 2, Stage 0 Complex 3 and Stage 0 Complex 4. The Stage I Complexes comprise Stage I Complex 1, Stage I Complex 2, Stage I Complex 3, Stage I Complex 4, Stage I Complex 5, Stage I Complex 6, Stage I Complex 7 and Stage I Complex 8. In some aspects, the breast cancer complex comprises a cancer peptide motif having an amino acid sequence selected from SEQ ID NOs: 1-122.

The invention also features an isolated polypeptide, which can be used as a marker specific for a disease, preferably cancer. The polypeptide may comprise a cancer peptide motif. A cancer peptide motif originates from a cancer peptide fragment (i.e. fragment of a larger cancer protein) that is sequestered by a circulatory serum albumin complex. The cancer peptide motif may have the same length as the cancer peptide fragment present in the serum albumin complex. Most likely the cancer peptide motif may have a shorter length than the original cancer peptide fragment. This is because the cancer peptide motif is recovered only after the digestion of the sequestered cancer peptide fragment with an enzyme such as trypsin which results in removing some amino acid residues at the carboxyl terminal end of the cancer peptide fragment. The removed amino acid residues are not recovered and therefore lost. Similarly, some of the amino acids of the cancer peptide fragment at the N-terminal end are also removed by the enzymatic digestion and not recovered. It is therefore to be expected that most cancer peptide motifs have shorter amino acid sequences when compared to their corresponding cancer peptide fragments. Since a cancer peptide motif originates from a cancer peptide fragment that is sequestered by serum albumin complex in a cancer or specific stage of a cancer, it can be used as a disease-specific or stage-specific marker. A cancer peptide motif may have an amino acid sequence selected from SEQ ID NOs: 1-122, preferably SEQ ID NOs: 44 and 46. Various cancer peptide motifs have been found to be associated with Stage 0, Stage I, or other stages of breast cancer. The inventive methods contemplate that additional serum albumin complexes comprising stage-specific breast cancer-associated proteins and polypeptides will be discovered and characterized over time. Probes specific for those polypeptides can be used in the methods to diagnose Stage 0, Stage I or other stages of breast cancer in accordance with the inventive methods.

The polypeptides of the invention may have any size fragments, preferably at least about 6, 10, 14, 20, 25, or 30 amino acids. A "polypeptide" refers to a peptide or protein comprising two or more amino acids joined to each other by peptide bonds or modified peptide bonds, i.e., peptide isosteres. Polypeptides may have short chains, commonly referred to as peptides, oligopeptides or oligomers, or long chains, generally referred to as proteins. Polypeptides may contain amino acids other than the 20 gene-encoded amino acids. Polypeptides may have amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

The polypeptides of the invention include addition variants (additional amino acids or amino acid chains added to either or both of the N-terminal or C-terminal end), and variants having a single or multiple amino acid substitutions, deletions, additions, or replacements may retain the biological properties of the base sequence (for example, a marker of one or more stages of breast cancer). The variants may have at least about 80%, 85%, 90%, 95% or 99% identity with a base sequence, for example, a sequence selected from SEQ ID NO: 1-127. Variants include fusions with another peptide or polypeptide such as a fusion partner, a protein tag or other chemical moiety.

Figure 15:
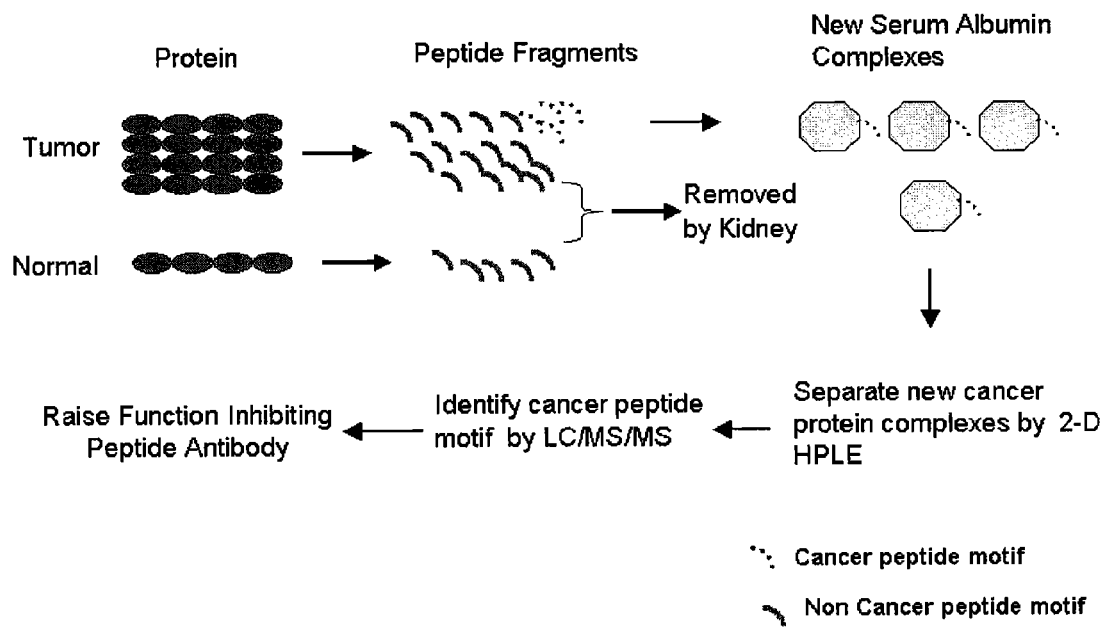
FIG. 15 shows one embodiment of identification and use of cancer peptide motifs.

According to the methods of the invention, a cancer peptide motif can be detected in a tumor or cancer protein (FIG. 15). In general, a cancer peptide motif represents only about 1 to 3% of a cancer protein. For example, Biomarker 4 (EEAS-PEAVAGVGFESK, SEQ ID NO: 44) has only 16 out of the 1,395 amino acid residues (~1.2%) of G-protein coupled receptor-associated sorting protein 1 (GASP-1). The cancer peptide motif can be detected because the corresponding cancer protein is degraded by proteolytic enzymes generating peptide fragments which are subsequently secreted into the bloodstream. Most of these peptide fragments are removed by kidney and disappeared from circulation quickly. Only very small number of the peptide fragments (or cancer peptide motifs) have high binding affinity for a pre-existing serum albumin complex and can form a new cancer protein complex. The newly-formed cancer protein complex (out of several hundred serum albumin complexes present in the circulation) is separated and detected by the methods of the invention. The amino acid sequence of the cancer peptide motif is then identified by LC/MS/MS. A corresponding peptide antibody is produced according to the methods of the invention.

The invention provides a method for detecting a low copy number polypeptide in a biological sample. A low copy number polypeptide may be a polypeptide having a concentration of, for example, less than $10^{-6}$, $10^{-8}$, $10^{-10}$, or $10^{-12}$ M in a biological sample. The low copy number polypeptide may comprise a cancer peptide motif. In general, the methods comprise obtaining a biological sample comprising a plurality of serum albumin complexes, optionally separating the biological sample into hydrophilic and hydrophobic fractions, separating the serum albumin complexes, digesting at least one separated serum albumin complex on the membrane with a protease, and detecting the polypeptide in the digested complex. In some aspects, the method may further comprise determining the amino acid sequence of the detected polypeptide or the detected cancer peptide motif.

The albumin complexes can be separated on a membrane by any means suitable in the art, including polyacrylamide gel electrophoresis followed by transfer to the membrane. Preferably, the separation is carried out directly on the membrane using membrane electrophoresis. The membrane electrophoresis is preferably two-dimensional membrane electrophoresis as described and exemplified herein. Any membrane suitable for separating serum albumin complexes can be used, including PVDF membranes.

The invention also provides kits for detecting a low copy number polypeptide in a biological sample. Such kits comprise one or more membranes suitable for a two-dimensional membrane electrophoresis, a protease, and instructions for using the kit in a method of detecting a low copy number polypeptide obtained from a biological sample. The kits can also comprise an agent that detects a disease-specific marker, for example, a probe such as an antibody that specifically binds to a particular polypeptide. The kits can also comprise reagents for sequencing polypeptides.

The invention provides a method of producing antibodies, comprising administering an effective amount of a cancer peptide motif or a longer polypeptide containing the cancer peptide motif of the invention to an immunologically competent host, and recovering immune sera or antibodies from the host. The polypeptide has at least about 6, 10, 14, 20, 25 or 30 amino acids. Preferably, the polypeptide has about 14-20 amino acids. Antibodies can also be made by culturing bone marrow or peripheral blood cells isolated from an immunologically competent host with an effective amount of a serum albumin complex or a polypeptide of the invention, isolating B cells that express an antibody that specifically binds to the polypeptide, and isolating antibodies produced by the B cells.

Cancer peptide fragments comprising cancer peptide motifs may be used for the development of highly specific "peptide antibodies" recognizing only a small region of the cancer protein (rather than the entire protein) for use in diagnostic kits for cancer detection and for providing specific targets for therapeutic treatment. Because the antibodies are raised against a very small region and not to the whole protein, they will be highly specific and not to cross-react with other protein in the body. For example, Biomarker 4 is directed against a 16-amino acid sequence (residue 850 to 865) of a 1,395 amino acid protein. Because only this short polypeptide motif is over-expressed in cancer cases, antibody against this segment will not cross-react with other normal proteins, thereby reducing the background noise level. Furthermore, only about 1% of the protein contains the newly discovered cancer peptide motif, antibodies directed against other regions of the protein (e.g., directed against an entire cancer protein as commonly used) will be unlikely to detect this specific peptide motif and therefore render them to be ineffective. Therapeutics targeting a cancer peptide motif sequence will be highly specific and to be expected to have much fewer side effects, if any. Therapeutics also include biomolecules (e.g., antibodies) that have high affinity for the newly identified cancer peptide motifs.

An isolated antibody that binds specifically to a cancer polypeptide comprising a cancer peptide motif may be obtained according to the methods of the invention. A rabbit antibody has been generated to bind specifically to a cancer polypeptide having an amino acid sequence selected from SEQ ID NOs: 44 and 123-127. The antibody may be used to detect an antigen (e.g., a cancer peptide motif, and its corresponding cancer protein) in a biological sample. An antibody may be incubated with the biological sample under conditions (e.g., 10 min. under room temperature) to permit formation of an antigen-antibody complex, which may be detected. The antigen in the biological sample may be quantified by separating the antigen-antibody complex on a membrane by electrophoresis (e.g., one-dimensional or two-dimensional electrophoresis on a blot membrane), and quantifying the antigen in the antigen-antibody complex spot.

An antibody of the present invention may be used to inhibit the growth of a cancer cell by applying the antibody to the cell. Suitable cancer cells include breast cancer cells, glioma cells, bladder cancers, colon cancer cells, esophagus cancer cells, hepatocellular carcinoma cells, larynx cancer cells, lung cancer cells, skin cancer cells, ovarian cancer cells, prostate cancer cells, pancreatic cancer cells, renal cancer cells, or stomach cancer cells, preferably breast cancer cells and glioma cells. The antibody may bind specifically to a cancer polypeptide comprising a cancer peptide motif having an amino acid sequence selected from SEQ ID NOs: 1-122. The cancer polypeptide may have an amino acid sequence selected from SEQ ID NOs: 44 and 123-127, preferably SEQ ID NOs: 44, 125 and 127, more preferably SEQ ID NOs: 44 and 127. The antibody may also be used to treat a cancer patient by administering an effective amount of the antibody to the subject, whereby the antibody inhibits tumor growth or cancer migration in the subject. Suitable tumors or cancer include breast cancer, glioma, bladder cancer, colon cancer, esophagus cancer, hepatocellular carcinoma, larynx cancer, lung cancer, skin cancer, ovarian cancer, prostate cancer, pancreatic cancer, renal cancer, and stomach cancer.

Any combination of antibodies of the present invention can be used to prepare an array. An array may comprise a plurality of antibodies, each of which binds specifically a cancer polypeptide of the present invention. In one embodiment, at least one antibody in the array binds specifically a cancer polypeptide comprising a cancer peptide sequence having an amino acid sequence selected from SEQ ID NOs: 1-122. In another embodiment, at least one antibody in the array binds specifically a cancer polypeptide having an amino acid sequence selected from SEQ ID NOs: 44 and 123-127, preferably SEQ ID NOs: 44 and 127. In yet another embodiment, at least one antibody in the array binds specifically a cancer polypeptide comprising a cancer peptide motif, wherein each cancer peptide motif is present in a breast cancer complex selected from the group consisting of Stage 0 Complexes, Stage I Complexes, Stage II Complexes, Stage III Complexes and Stage IV Complexes. The antibody array of the present invention may be used in an assay to diagnose cancer (e.g., breast cancer) and/or an assay to differentiate among cancer stages (e.g., breast cancer stages).

Methods for preparing polypeptide arrays are known in the art. Arrays of any combination of polypeptides of the present invention can be prepared. The array may comprise a plurality of (e.g., two, three, four, five or more) cancer polypeptide of the present invention. In one aspect, an array may comprise a plurality of breast cancer peptide motifs, each of which is present in a beast cancer complex selected from Stage 0 Complexes (e.g., Stage 0 Complex 1, Stage 0 Complex 2, Stage 0 Complex 3, and/or Stage 0 Complex 4), Stage I Complexes (e.g., Stage I Complex 1, Stage I Complex 2, Stage I Complex 3, Stage I Complex 4, Stage I Complex 5, Stage I Complex 6, Stage I Complex 7, and/or Stage I Complex 8), Stage II Complexes, Stage III Complexes and Stage IV Complexes. The arrays may specifically exclude a cancer polypeptide of the present invention.

Any suitable probe specific for detecting breast cancer peptide markers for any stage (e.g., Stage 0, Stage I, Stage II, Stage III and/or Stage IV) can be used for diagnosing or staging breast cancer in a subject. Antibodies that specifically bind to such markers are preferred. Monoclonal antibodies are most preferred, but polyclonal antibodies and immune sera can also be used. Multiple probes can be used on a single sample to detect multiple polypeptide markers.

Various terms relating to the systems, methods, and other aspects of the present invention are used throughout the specification and claims. Such terms are to be given their ordinary meaning in the art unless otherwise indicated.

As used in this specification and the appended claims, the singular forms "a," "an," and "the" include plural referents unless the content clearly dictates otherwise. Thus, for example, reference to "a complex" includes a combination of two or more complexes, and the like.

The term "about" as used herein when referring to a measurable value such as an amount, a percentage, and the like, is meant to encompass variations of ±20% or ±10%, more preferably ±5%, even more preferably ±1%, and still more preferably ±0.1% from the specified value, as such variations are appropriate to perform the disclosed methods.

The following examples are provided to describe exemplary aspects of the invention in greater detail. They are intended to illustrate, not to limit, the invention.

Example 1

Separation of Protein Complexes Using Two-Dimensional Membrane Electrophoresis or 2-D HPLE An innovative procedure for separation and detection of protein complexes containing the newly generated breast cancer markers was developed. To retain protein complexes containing low-abundance breast cancer markers, the electrophoresis process was carried out under non-denaturing conditions. Unlike the commonly used two-dimensional polyacrylamide gel electrophoresis (2-D PAGE), proteins and their complexes are separated directly on polyvinylidene fluoride (PVDF) membrane rather than in a gel. The term "2-D HPLE" (2-D High Performance Liquid Electrophoresis) will be used subsequently to described the 2-D membrane electrophoresis process. Thus, the 2-D HPLE procedure not only separates serum albumin complexes but also eliminates the blotting step required for Western blotting analysis when the conventional 2-D PAGE is used.

The 2-D HPLE is carried out using a horizontal electrophoresis unit from materials that are compatible with the water-miscible organic solvent buffers such as glass.

The unit contains two buffer chambers located at opposite ends of the unit. Electrodes are located adjacent to buffer chambers, so that the platinum wires extend into the buffer chambers. A fixed, raised platform separates the two buffer chambers to prevent fluid communication between the chambers when they are filled with the buffer. A filter paper wick previously wetted with the water-miscible organic solvent buffer rests on the raised platform. The protein sample is usually mixed with a wetting agent such as ε-caprolactone before electrophoresis. The protein sample was then spotted on PVDF membrane and allowed to dry. This is followed by wetting the membrane with the same water-miscible organic solvent buffer used for electrophoresis. The membrane is then placed directly on top of the filter paper wick. The membrane is then covered with a glass plate (top glass plate). To prevent inadvertent electric shock during electrophoresis, a cover plate is placed over the entire unit before voltage is applied across the electrodes.

To illustrate the finding that proteins are separated on PVDF membrane according to their isoelectric points (pI) without the need of either carrier ampholytes or preformed pH gradients, a mixture of six proteins with pI's ranging from 3.6 to 9.6 were electrophoresed one dimensionally. Since these proteins are not known to form complexes, they are separated as single proteins. The result of protein separation in a water-miscible low conductivity organic solvent buffer having a pH of 5.0 is shown in FIG. 1A.

The composition of this low conductivity buffer was as follows: 28% ethylene cyclic carbonate, 20% salicylaldehyde, 12% furfuryl alcohol, 8% 1,3-butanediol, 16% dimethylformamide, and 16% dimethylacetamide (v/v). The pH of the buffer was adjusted to 5.0 with 12 M formic acid. It should be noted that proteins such as cytochrome C (pI=9.6) that are more than 4 pI units from the pH of the solvent buffer can be effectively separated. Lentil lectin which contains three proteins with pI's of 8.4, 8.6 and 8.8 were separated into three bands. Rate of protein migration on the membrane was exceedingly fast, with cytochrome C traveled at a rate of about 1 cm/min in this pH 5.0 solvent buffer.

Because of fast protein migration, electrophoretic separation of proteins on PVDF membrane took only 6 minutes when carried out at room temperature at 3.5 kV. Similarly, a water-miscible organic solvent buffer with a pH of 8.0 was used to separate the same protein mixture (FIG. 1B). This buffer had the following composition: 44% propylene carbonate, 12% formamide, 12% furfuryl alcohol, 16% 1,3-butanediol, and 16% N-methyl pyrrolidinone (v/v). The pH of this buffer was brought to 8.5 with 0.5 M piperazine dissolved in water.

Protein mixture was separated again in 6 minutes at 3.5 kV with proteins separated pretty much according to their isoelectric points (FIG. 1B). Since proteins were separated quickly in the membrane electrophoresis in two different water-miscible organic solvent systems at pH 5.0 and 8.0 under non-denaturing conditions, a 2-D electrophoresis system on PVDF membrane was developed to separate albumin complexes.

The Bordier procedure for separation of membrane proteins was modified to separate human serum albumin into hydrophilic and hydrophobic fractions (Bordier (1981) J. Biol. Chem. 256:1604-07). Six µg of total protein were spotted at the middle of a PVDF membrane (9 cm×13 cm). Upon completion of the first dimension separation at pH 5.0, the membrane was marked to ensure proper orientation and washed several minutes in deionized $H_2O$ to remove the first dimension solvent. After equilibration with the second dimension solvent buffer (pH 8.0), the membrane was then placed at 90° from its original position to start the second dimension which took about 6 minutes to complete. All operations were carried out at room temperature.

At the end of the second dimension separation, the membrane was removed, washed with deionized $H_2O$ and stained with 0.05% Reactive brown 10 in water. We have previously reported that Reactive Brown 10 can detect the separated proteins and their complexes within 10 seconds after dipping into the dye solution with a sensitivity of detection comparable to that of silver stain (Yonan et al. (2005) Anal. Biochemistry 338:159-161). The very high sensitivity of Reactive brown 10 allows a great reduction in the amount of protein sample required for carrying out the 2-D HPLE (6 µg of protein in 2-D HPLE vs. approx. 100 µg of protein in 2-D PAGE).

The separation of serum albumin complexes on PVDF membranes is based on their net charge or isoelectric points (pI). The rationale of this approach to detect new cancer markers (or cancer peptide motifs) is that the association of a cancer protein (or its fragments) with a pre-existing albumin complex changes its pI and this newly formed complex migrates to a different location on the PVDF membrane. The change in the migration rate allows easy detection of newly generated albumin complex containing the cancer markers (or cancer peptide motifs) on the PVDF membrane.

Example 2

Separation of Serum Albumin Complexes from Normal (Healthy) Individuals

A prerequisite in identifying serum markers associated with the initiation and progression of a disease is to be able to separate the albumin complexes and to establish a 2-D albumin complex profile of normal (healthy) individuals. The profile can then serve as a reference for the detection of disease protein-containing albumin complexes.

Figure 2B:
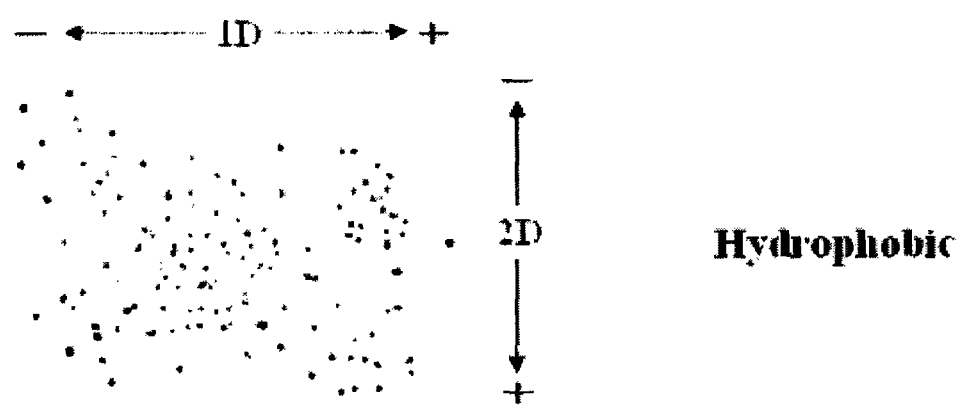

To eliminate the crowding of albumin complex spots, serum samples were separated into hydrophilic and hydrophobic fractions by using the detergent Triton X-114 before electrophoresis (Bordier (1981) J. Biol. Chem. 256: 1604-07). Six µg of total protein from each fraction were spotted at the middle of a PVDF blot membrane (9 cm×13 cm). Upon completion of the first dimension separation at pH 5.0 which took 6 minutes to complete, the membrane was washed several minutes in deionized $H_2O$ to remove the first dimension solvent. After equilibration with the second dimension solvent buffer (pH 8.0), the membrane was then placed at 90° from its original position to start the second dimension which also took about 6 minutes to complete. The entire 2-D HPLE on PVDF membrane took only 40 minutes (including the two washing steps and subsequent staining of proteins) and required just 6 µg of sample. The albumin complexes in the hydrophobic serum fraction were resolved into about 150 very compact spots (FIG. 2).

Example 3

Albumin Complexes Associated with Earliest Stage (Stage 0) Breast Cancer

Serum samples from patients with stage 0, I, II, III, or IV breast cancer as well as normal controls were purchased from the Lombardi Comprehensive Cancer Center at Georgetown University. They house an extensive serum and tumor repository of breast cancer patients.

Figure 3A:
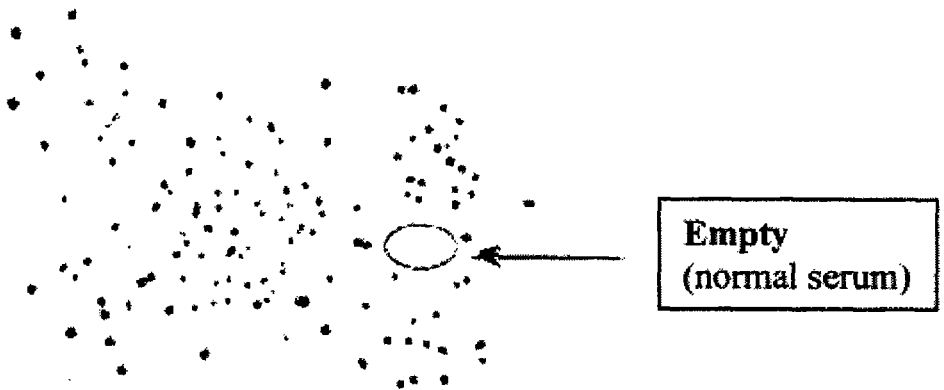
FIGS. 3A-3C show separation profiles of serum albumin complexes in serum samples from a healthy individual (A), a patient with Stage 0 breast cancer (B), and a patient with Stage I breast cancer (C). Arrows indicate Cluster 0 of stage 0 complexes (B) and Cluster 1 of stage I complexes (C).
Figure 3B:
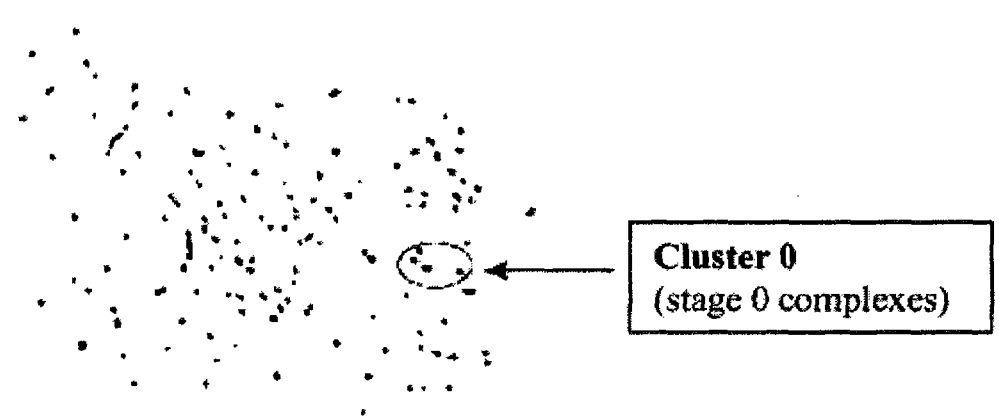

As indicated earlier, 2-D HPLE separates serum albumin complexes and can detect any newly formed cancer-protein containing albumin complexes among several hundred pre-existing complexes due to change in their surface charges which cause them to migrate to different locations on the PVDF membrane. This altered electrophoretic mobility allows for the detection of cancer peptide motif-containing albumin complexes associated with very early stage of breast cancer (Stage 0) before the disease is detected by mammography. Likewise, albumin complexes containing cancer peptide motifs for other more advanced stages (Stages I to IV) were also detected. After 2-D HPLE separating the hydrophobic serum albumin fractions, the appearance of stage-specific cancer protein complex clusters can be correlated with the pathological stages of breast cancer (Stages 0 to IV). The following Stage-specific cancer protein complex markers were found:

1) Markers for Stage 0 (precancerous): In the healthy (cancer-free) individual, the area circled in FIG. 3A is empty. The transformation of a healthy breast to Stage 0 is associated with the appearance of a number of new albumin complex spots. Of particular interest is a new cluster (Cluster 0) of four cancer peptide motif-containing albumin complexes that were missing in the normal hydrophobic serum (FIG. 3B). These four new albumin complexes constitute only less than 3% of total albumin complexes and can only be detected by resolution of albumin complexes using the 2-D HPLE procedure.

Figure 3C:
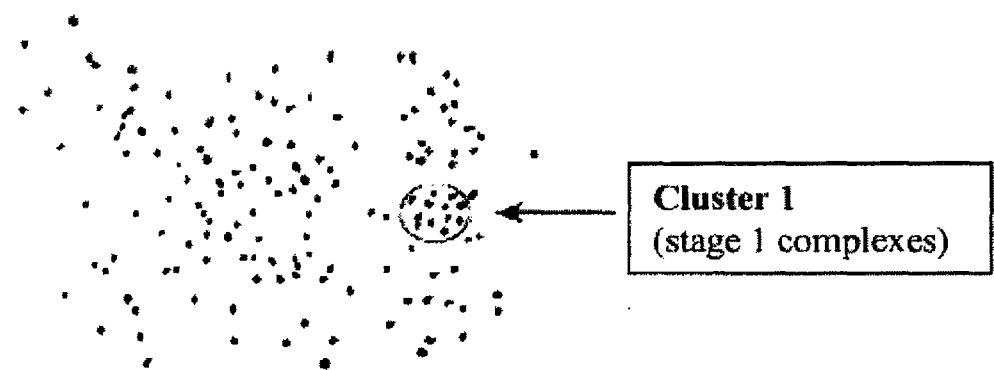

2) Markers for Stage I breast cancer (Cluster 1): As shown in FIG. 3C, the progression of breast cancer from Stage 0 to Stage I is correlated with the appearance of 8 more cancer peptide motif-containing albumin complexes in the same cluster (now becomes Cluster 1). The appearance of this 12 albumin-complex cluster signals that the cancer has already progressed from Stage 0 to Stage I.

Figure 4A:
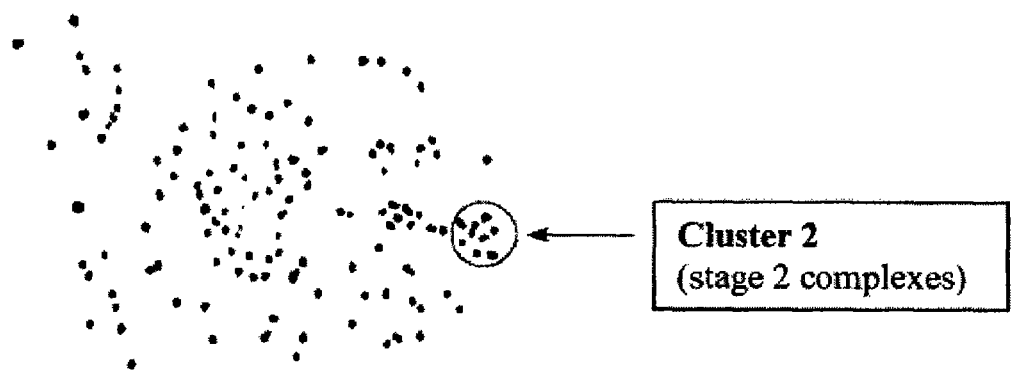
FIG. 4A-4C show separation profiles of serum albumin complexes in serum samples from a patient with Stage II breast cancer (A), Stage III breast cancer (B), or Stage IV breast cancer (C). Arrows indicate Cluster 2 of stage II complexes (A), Cluster 3 of stage III complexes (B), and Cluster 4 of stage IV complexes (C).

3) Markers for Stage II breast cancer (Cluster 2): The appearance of a new cluster of 9 cancer peptide motif-containing albumin complexes (Cluster 2) to the right of the Stage I cluster indicates that the cancer has advanced from Stage I to Stage II (FIG. 4A).

Figure 4B:
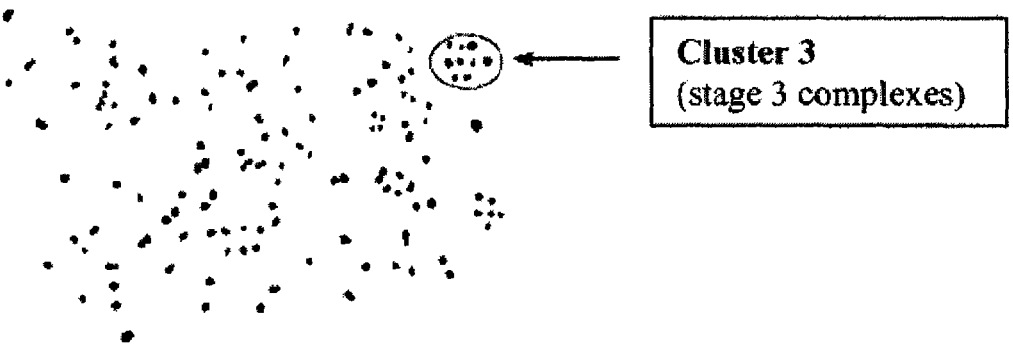

4) Markers for Stage III breast cancer (Cluster 3): The presence of a new cluster of 9 cancer peptide motif-containing albumin complexes (Cluster 3) at the upper right-hand corner (which was empty in Stage II breast cancer) marks the progression of cancer from Stage II to Stage III (FIG. 4B).

Figure 4C:
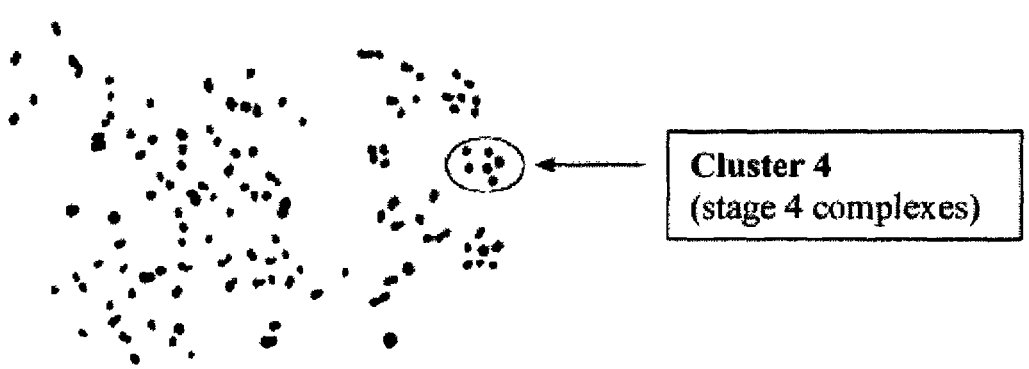

5) Markers for Stage IV breast cancer (Cluster 4): The appearance of a new cluster of 6 cancer peptide motif-containing protein complexes (Cluster 4) underneath the Stage III cluster (FIG. 4C) signals that the cancer has advanced to Stage IV.

From these results, it is evident that as breast cancer progresses, more cancer peptide motif-containing protein complexes are produced resulting in an increase in the number of new albumin complexes with altered mobility on PVDF membrane. For example, Stage III breast cancer serum contains 3 clusters (Cluster 3 and remnant spots from Clusters 1 and 2). Stage II breast cancer serum contains 2 clusters. These stage-specific albumin complex cluster profiles are highly reproducible.

In addition to breast cancer, over 200 serum samples from other cancers were analyzed, including pancreatic, liver, and skin cancers. None of these cancers exhibit protein complex clusters that overlap with the five clusters (Clusters 0 to 4) associated with the five different stages of breast cancer (Stages 0 to 4) reported here. Therefore, these findings suggest that Stage-specific clusters (and the protein complexes in the cluster) are unique and can be employed for identifying the stage of breast cancer.

The resolution of albumin complexes paves the way for the identification of cancer peptide motif-containing associated with initiation (earliest stage) and progression of breast cancer. As indicated earlier, the transformation of a healthy breast to Stage 0 is associated with the appearance of a number of new cancer peptide motif-containing albumin complex spots (FIG. 3). Of particular interest is a new cluster of four albumin complexes that were missing in the normal hydrophobic serum (empty circle in FIG. 3A). These four breast cancer peptide motif-containing complexes represent only 3% of total serum albumin complexes (4 out of about 150 complexes). Because 97% of the proteins were present in both normal and breast cancer individuals, these cancer peptide motif biomarkers could not be detected without first separating the cancer serum albumin complexes using 2-D HPLE procedure.

Figure 5:
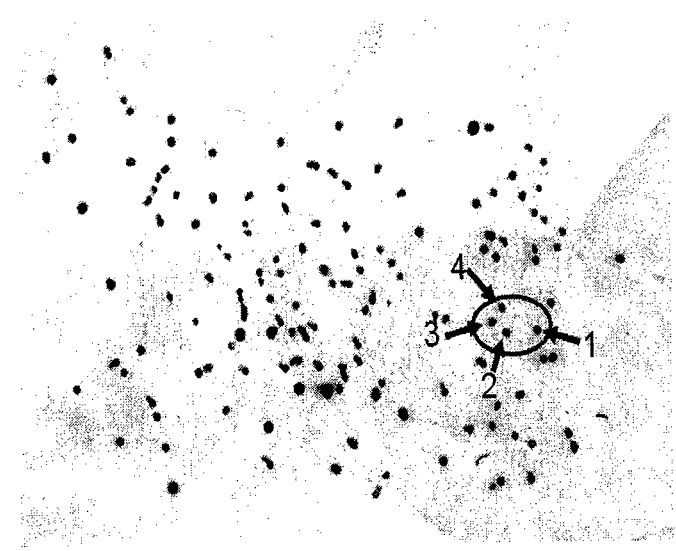
FIG. 5 shows Stage 0 Complexes 1-4 in Cluster 0 shown in FIG. 3B selected for mass spectrometric analysis.

Cancer peptide motif biomarkers associated with the 4 newly produced Stage 0 albumin complexes (shown in FIG. 5) were analyzed subjecting to on-membrane digestion with trypsin and the peptides identified by liquid chromatography with tandem spectrometry sequencing of individual peptides (LC/MS/MS). Protein identities are determined from data base searches of virtual tryptic peptide data bases or fragmentation spectra of tryptic peptides. The Wistar Proteomic Facility in Philadelphia has developed a tryptic digest procedure for identification of proteins and peptide fragments present in serum albumin complexes on PVDF membrane.

In brief, the cancer peptide motif biomarkers from separated albumin complex spot of interest was excised from the PVDF membrane and destained. It was reduced using 20 mM (2-carboxyethyl)phosphine hydrochloride (TCEP) in 25 mM ammonium bicarbonate followed by alkylation with 40 mM iodoacetamide in 25 mM ammonium bicarbonate. Digestion was carried out with a solution of 50 µl 0.02 µg/µl modified trypsin (Promega) in 30% acetonitrile and incubated overnight. The next morning the supernatant was removed to a clean tube and 50 µl of 40 mM ammonium bicarbonate/30% acetonitrile was added for 30 min w/shaking at 37° C. The supernatants were combined and 8 µl of neat Acetic Acid was added.

A portion of the combined digest solution (8 µl) was used for mass spectrometric analysis using a capilliary HPLC with a 75 µm nanocolumn and a Thermo Fisher LTQ-Orbi-Trap XL, a hybrid system combining LTQ linear ion trap mass spectrometer with the Orbi mass analyzer. The resulting masses and spectra were searched against a custom database using TurboSequest with the Proteomics Browser interface with detailed inspection of selected peptides using Fuzzy Ions (William Lane, Harvard Microchemistry and Proteomics Analysis Facility). LC-MS/MS, database searching and analysis were performed in the Wistar Institute Proteomics Core Facility. The inventors would particularly like to acknowledge the assistance of Thomas Beer and Kaye Speicher in the Proteomics Facility for performing these analyses.

Table 1 shows the cancer peptide motifs that are associated with the four albumin complexes. For each cancer peptide motif, the name is followed by the ID of its corresponding protein (i.e., the protein that contains the cancer peptide motif) and either the number of cancer peptide motifs detected or, if it is a single peptide motif, the tryptic peptide amino acid sequence present in the cancer peptide motif.

TABLE 1

Mass spectrophotometric analysis of components of cancer peptide motifs and their corresponding proteins in Stage 0 (and Early Stage I) breast cancer protein complexes Stage 0 (complex 1)

_HOMO Serum albumin, a6nbz8 (16 fragments)

_HOMO Dermcidin precursor (Preproteolysin), p81605 (5 fragments)

_HOMO Prolactin-induced protein, a0a9f3 TVQIAAVVDVIR (SEQ ID NO: 1) and FYTIEILKVE (SEQ ID NO: 2)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Golgi reassembly-stacking protein 2, q9h8y8 TPVSEK (SEQ ID NO: 5)

_HOMO Mucin-like protein 1 precursor, q96dr8 WVGDLPNGR (SEQ ID NO: 6)

_HOMO Nuclear protein Hcc-1, p82979 DDEKLK (SEQ ID NO: 7)

_HOMO Zinc finger CCCH domain-containing protein 11A, o75152 IDSEIK (SEQ ID NO: 8)

Stage 0 (complex 2)

_HOMO Serum albumin, a6nbz8 (16 fragments)

_HOMO Dermcidin precursor (Preproteolysin), p81605 ENAGEDPGLAR (SEQ ID NO: 9), and LGKDAVEDLESVGK (SEQ ID NO: 10)

_HOMO Cleavage stimulation factor 64 kDa subunit, p33240-2 ATEEQLK (SEQ ID NO: 4)

_HOMO A-kinase anchor protein 13 (AKAP 13) (Breast cancer nuclear receptor-binding auxiliary protein), q12802 VGPVSLPR (SEQ ID NO: 3)

_HOMO Golgi reassembly-stacking protein 2, q9h8y8 TPVSEK (SEQ ID NO: 5)

_HOMO Prolactin-induced protein, a0a9f3 TVQIAAVVDVIR (SEQ ID NO: 1)

_HOMO Alpha-fetoprotein precursor, p02771 IYEIAR (SEQ ID NO: 11)

_HOMO Mucin MUC5B, o00446 TTPTVISWK (SEQ ID NO: 12)

_HOMO Disco-interacting protein 2 homolog C, q9y2e4 IVEVSR (SEQ ID NO: 13)

_HOMO IQ domain-containing protein G, q9h095 EMNLEGTNLDKLPMAS (SEQ ID NO: 14)

_HOMO TBC1 domain family member 12 o60347 TEGVSVADREASLELIKLDISR (SEQ ID NO: 15)

_HOMO Tripartite motif-containing 27, q5rja8 LEELDLAIYNS (SEQ ID NO: 16)

_HOMO G2/M phase-specific E3 ubiquitin-protein ligase. q7I622 NLSLNS (SEQ ID NO: 17)

Stage 0 (complex 3)

_HOMO Serum albumin, a6nbz8 (15 fragments)

_HOMO Hornerin, q5dt20 (14 fragments)

_HOMO Desmoglein-1 precursor, q02413 (3 fragments)

_HOMO Junction plakoglobin, p14923 (2 fragments)

_HOMO Dermcidin precursor (Preproteolysin), p81605 ENAGEDPGLAR (SEQ ID NO: 9)

_HOMO Cleavage stimulation factor 64 kDa subunit, p33240-2 ATEEQLK (SEQ ID NO: 4)

TABLE 1-continued

Mass spectrophotometric analysis of components of cancer peptide motifs and their corresponding proteins in Stage 0 (and Early Stage I) breast cancer protein complexes _HOMO A-kinase anchor protein 13 (AKAP 13) (Breast cancer nuclear receptor-binding auxiliary protein) q12802 VGPVSLPR (SEQ ID NO: 3)

_HOMO Alpha-fetoprotein precursor, p02771 IYEIAR (SEQ ID NO: 11)

_HOMO Afamin precursor, p43652 LSQKFPK (SEQ ID NO: 18)

_HOMO Eukaryotic translation initiation factor 4E transporter, q9nra8 LSSSSVPSADR (SEQ ID NO: 19)

_HOMO Disco-interacting protein 2 homolog C, q9y2e4 IVEVSR (SEQ ID NO: 13)

_HOMO Ubiquitin carboxyl-terminal hydrolase, q05c98 QGLPGTSNSNSSRSGSQR (SEQ ID NO: 20)

_HOMO Exportin-7, q9uia9 TYTPEVTK (SEQ ID NO: 21)

_HOMO Transcriptional adapter 2-beta, q86tj2 LAEVSPLR (SEQ ID NO: 22)

_HOMO Protein kinase C-binding protein 1, a8k6I3 DSEGTPVNK (SEQ ID NO: 23)

_HOMO cDNA FLJ76883, highly similar to *Homo sapiens* FKSG44 gene (FKSG44) a8k6I3 DSEGTPVNK (SEQ ID NO: 23)

Stage 0 (complex 4)

_HOMO Serum albumin, a6nbz8 (14 fragments)

_HOMO Dermcidin precursor (Preproteolysin), p81605 (12 fragments)

_Cleavage stimulation factor 64 kDa subunit, p33240-2 ATEEQLK (SEQ ID NO: 4)

_HOMO A-kinase anchor protein 13 (AKAP 13) (Breast cancer nuclear receptor-binding auxiliary protein) q12802 VGPVSLPR (SEQ ID NO: 3)

_HOMO Hornerin, q86yz3 GPYESGSGHSSGLGHR (SEQ ID NO: 24)

_HOMO Disco-interacting protein 2 homolog C, q9y2e4 IVEVSR (SEQ ID NO: 13)

_HOMO WD repeat-containing protein 19, q8nez3 LAGVAQMSIR (SEQ ID NO: 25)

_HOMO Antithrombin-III precursor q5r5a3 LPGIVAEGR (SEQ ID NO: 26)

Table 2 shows the list of cancer peptide motifs (and their peptide sequences) from the above Stage 0 (and early Stage I) breast cancer complexes.

TABLE 2

List of cancer peptide motifs from Stage 0 (and Early Stage I) breast cancer complexes 1) Dermcidin precursor (Preproteolysin) (ENAGEDPGLAR (SEQ ID NO: 9)), (LGKDAVEDLESVGK (SEQ ID NO: 10)), (DAVEDLESVGK (SEQ ID NO: 27)), (YDPEAASAPGSGNPCHEASAAQK (SEQ ID NO: 28)), (GAVHDVKDVLDSV (SEQ ID NO: 29))

2) A-kinase anchor protein 13 (VGPVSLPR (SEQ ID NO: 3))

3) Cleavage stimulation factor 64 kDa subunit (ATEEQLK (SEQ ID NO: 4))

4) Prolactin-induced protein (TVQIAAVVDVIR (SEQ ID NO: 1)), (FYTIEILKVE (SEQ ID NO: 2))

5) Mucin-like protein 1 precursor (WVGDLPNGR (SEQ ID NO: 6))

6) Mucin MUC5B (TTPTVISWK (SEQ ID NO: 12))

TABLE 2-continued

List of cancer peptide motifs from Stage 0 (and Early Stage I) breast cancer complexes 7) Eukaryotic translation initiation factor 4E transporter (LSSSSVPSADR (SEQ ID NO: 19))

8) Golgi reassembly-stacking protein 2 (TPVSEK (SEQ ID NO: 5))

9) Alpha-fetoprotein precursor, p02771 (IYEIAR (SEQ ID NO: 11))

10) Nuclear protein Hcc-1, p82979 (DDEKLK (SEQ ID NO: 7))

11) Zinc finger CCCH domain-containing protein 11A (IDSEIK (SEQ ID NO: 8))

12) G2/M phase-specific E3 ubiquitin-protein ligase (NLSLNS (SEQ ID NO: 30))

13) Transcriptional adapter 2-beta (LAEVSPLR (SEQ ID NO: 22))

14) Protein kinase C-binding protein 1 (DSEGTPVNK (SEQ ID NO: 23))

15) WD repeat-containing protein 19 (LAGVAQMSIR (SEQ ID NO: 25))

16) Dynein heavy chain 8, axonemal (FEVEVTK (SEQ ID NO: 31))

17) Disco-interacting protein 2 homolog C (IVEVSR (SEQ ID NO: 13))

18) IQ domain-containing protein G (EMNLEGTNLDKLPMAS (SEQ ID NO: 14))

19) TBC1 domain family member 12 (TEGVSVADREASLELIKLDISR (SEQ ID NO: 15))

20) Tripartite motif-containing 27 (LEELDLAIYNS (SEQ ID NO: 16))

21) Ubiquitin carboxyl-terminal hydrolase (QGLPGTSNSNSSRSGSQR (SEQ ID NO: 20))

22) Exportin-7 (TYTPEVTK (SEQ ID NO: 21))

23) cDNA FLJ76883, highly similar to FKSG44 gene (FKSG44) (DSEGTPVNK (SEQ ID NO: 23))

Analysis of other Stage 0 and Early Stage 1 breast cancer complexes revealed the presence of additional cancer peptide motifs. These cancer peptide motifs (with the amino acid sequences) are listed in Table 3 below:

TABLE 3

List of additional cancer peptide motifs from mass spectrometric analysis of other Stage 0 (and Early Stage I) breast cancer complexes 1) Vacuolar protein sorting-associated protein 54 (TRELEEISQQKNAAKDNSLDTEV (SEQ ID NO: 32))

2) Transformation/transcription domain-associated protein (GLSVDSAQEVK (SEQ ID NO: 33))

3) SERPINB12 protein (DAINAETVLVLVNAVYFK (SEQ ID NO: 34)), (NIFFSPLSLSAALGMVR (SEQ ID NO: 35)), (IGFIEEVKAQILEMR (SEQ ID NO: 36))

4) Nuclear receptor coactivator 5 (EEIARQA (SEQ ID NO: 37))

5) Zinc finger and SCAN domain-containing protein 29 (LAILSQTEFYEALR (SEQ ID NO: 38))

6) Histone-lysine N-methyltransferase, H3 lysine-79 specific (FISAAAVPPGSLLSGPGLAPAASSAGGAASSAQTHR (SEQ ID NO: 39))

Example 4

Figure 6:
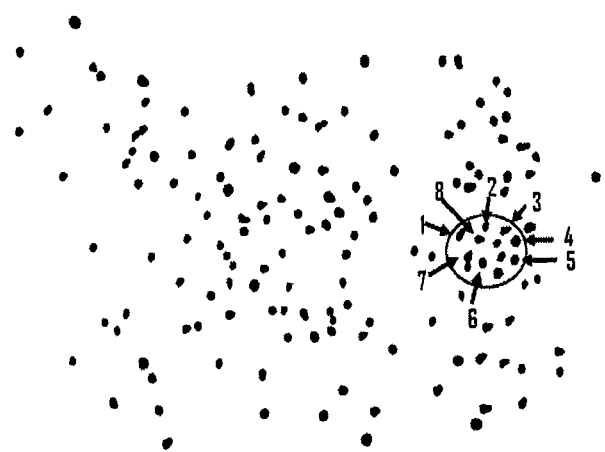
FIG. 6 shows Stage I Complexes 1-8 in Cluster 1 shown in FIG. 3C selected for mass spectrometric analysis.

Cancer Motif-Containing Albumin Complexes Associated with Stage I of Breast Cancer As shown in FIG. 4, the progression of breast cancer from Stage 0 to Stage I is correlated with the appearance of 12 cancer peptide motif-containing albumin complexes in the same cluster. The appearance of this 12 albumin-complex cluster signals that the cancer has already progressed from Stage 0 to Stage I. Table 4 shows the cancer peptide motifs associated with the eight albumin complexes (see FIG. 6). For each cancer peptide motif, the name is followed by the ID of its corresponding protein (i.e., the protein that contains the cancer peptide motif) and either the number of cancer peptide motifs detected or, if it is a single peptide motif, the tryptic peptide amino acid sequence present in the cancer peptide motif.

TABLE 4

Mass spectrophotometric analysis of components of Stage I complexes

Stage I (complex 1)

_HOMO Serum albumin, a6nbz8 (14 fragments)

_HOMO A-kinase anchor protein 13 (AKAP 13) (Breast cancer nuclear receptor-binding auxiliary protein) q12802 (2 fragments)

_HOMO Golgi reassembly-stacking protein 2, q9h8y8 (2 fragments)

_HOMO Dermcidin precursor (Preproteolysin), p81605 KENAGEDPGLAR (SEQ ID NO: 40)

_HOMO Cleavage stimulation factor 64 kDa subunit, p33240-2 ATEEQLK (SEQ ID NO: 4)

_HOMO Afamin precursor, p43652 LSQKFPK (SEQ ID NO: 18)

_HOMO U3 small nucleolar ribonucleoprotein protein IMP3, q9nv31 MEDFVTWVDSSK (SEQ ID NO: 41)

_HOMO Heat shock 105 kDa/110 kDa protein 1, q5tbm7 SVNEVMEWMNNVMNAQ (SEQ ID NO: 42)

_HOMO KIAA0861 protein, o94942 LATAELPR (SEQ ID NO: 43)

_HOMO G-protein coupled receptor-associated sorting protein 1, q5jy77 EEASPEAVAGVGFESK (SEQ ID NO: 44)

Stage I (complex 2)

_HOMO Serum albumin, a6nbz8 (22 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Golgi reassembly-stacking protein 2, q9h8y8 TPVSEK (SEQ ID NO: 5)

_HOMO Disco-interacting protein 2 homolog C, q9y2e4 IVEVSR (SEQ ID NO: 13)

_HOMO Dynein heavy chain 8, axonemal, q96jb1 FEVEVTK (SEQ ID NO: 31)

_HOMO Afamin precursor, p43652 LSQKFPK (SEQ ID NO: 18)

_HOMO Heat shock 105 kDa/110 kDa protein 1, q5tbm7 SVNEVMEWMNNVMNAQ (SEQ ID NO: 42)

_HOMO SH2B adaptor protein 2, upi000022d3dd TELSCTRGGCLASR (SEQ ID NO: 45)

_HOMO Vacuolar protein-sorting-associated protein 36, q86vn1 DGEEKIK (SEQ ID NO: 46)

_HOMO E3 ubiquitin-protein ligase BRE1B, o75150 EGPSLGPPP (SEQ ID NO: 47)

_HOMO Zinc finger protein ubi-d4, q92785 RGAPDPRVDDDSLGEFPVTN (SEQ ID NO: 48)

TABLE 4-continued

Mass spectrophotometric analysis of components of Stage I complexes

Stage I (complex 3)

_HOMO Serum albumin, a6nbz8 (21 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Golgi reassembly-stacking protein 2, q9h8y8 TPVSEK (SEQ ID NO: 5)

_HOMO Alpha-fetoprotein precursor, p02771 IYEIAR (SEQ ID NO: 11)

_HOMO Dynein heavy chain 8, axonemal, q96jb1 FEVEVTK (SEQ ID NO: 31)

_HOMO Tripartite motif-containing protein 32, q13049 PKGGGYSVLIR (SEQ ID NO: 49)

_HOMO Heat shock 105 kDa/110 kDa protein 1, q5tbm7 SVNEVMEWMNNVMNAQ (SEQ ID NO: 42)

_HOMO Isoform 2 of O60449, o60449-2 GADMISIHNEEENAFILDTLK (SEQ ID NO: 50)

_HOMO Docking protein 3 (Downstream of tyrosine kinase 3), upi0000d616c3 GPALLVLGPDAIQLR (SEQ ID NO: 51)

_HOMO Peroxisomal proliferator-activated receptor A interacting complex 285, a7e2c9 FAPSVVQ (SEQ ID NO: 52)

Stage I (complex 4)

_HOMO Serum albumin, a6nbz8 (22 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Alpha-fetoprotein precursor, p02771 IYEIAR (SEQ ID NO: 11)

_HOMO Afamin precursor, p43652 LSQKFPK (SEQ ID NO: 18)

_HOMO Dynein heavy chain 8, axonemal, q96jb1 FEVEVTK (SEQ ID NO: 31)

_HOMO Junction plakoglobin, p14923 NLALCPANHAP (SEQ ID NO: 53)

_HOMO U3 small nucleolar ribonucleoprotein protein IMP3, q9nv31 MEDFVTWVDSSK (SEQ ID NO: 41)

_HOMO DNA-binding protein SATB1, q01826 MQNFLQLPEAERDR (SEQ ID NO: 54)

_HOMO Tripartite motif-containing protein 2, q9c040 DGELCK (SEQ ID NO: 55)

_HOMO Peptidyl-prolyl cis-trans isomerase, q8n1e6 QITDSSLGRIAQ (SEQ ID NO: 56)

_HOMO Rho GTPase-activating protein 29, q52Iw3 VVDQGCFPK (SEQ ID NO: 57)

_HOMO Ubiquitin carboxyl-terminal hydrolase, a2rue3 PDGASCQGQPALHSENPFAKANGLPGK (SEQ ID NO: 58)

_HOMO BRCA1 associated RING domain 1, a0avn2 ELAVILK (SEQ ID NO: 59)

Stage I (complex 5)

_HOMO Serum albumin, a6nbz8 (24 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

TABLE 4-continued

Mass spectrophotometric analysis of components of Stage I complexes

_HOMO Disco-interacting protein 2 homolog C, q9y2e4 IVEVSR (SEQ ID NO: 13)

_HOMO Ubiquitin carboxyl-terminal hydrolase, q05c98 QGLPGTSNSNSSRSGSQR (SEQ ID NO: 20)

_HOMO U3 small nucleolar ribonucleoprotein protein IMP3, q9nv31 MEDFVTWVDSSK (SEQ ID NO: 41)

_HOMO DNA-binding protein SATB1, q01826 MQNFLQLPEAERDR (SEQ ID NO: 54)

_HOMO Heat shock 105 kDa/110 kDa protein 1, q5tbm7 SVNEVMEWMNNVMNAQ (SEQ ID NO: 42)

_HOMO Peptidyl-prolyl cis-trans isomerase, q8n1e6 QITDSSLGRIAQ (SEQ ID NO: 56)

_HOMO Rho GTPase-activating protein 29, q52Iw3 VVDQGCFPK (SEQ ID NO: 57)

_HOMO Zinc finger CCCH domain-containing protein 4, q9upt8 ASPSGDASPPATAPYDPR (SEQ ID NO: 60)

_HOMO RNA U small nuclear RNA export adapter protein, q9h814 ILGMEGTIDR (SEQ ID NO: 61)

Stage I (complex 6)

_HOMO Serum albumin, a6nbz8 (25 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Golgi reassembly-stacking protein 2, q9h8y8 TPVSEK (SEQ ID NO: 5)

_HOMO Dynein heavy chain 8, axonemal, q96jb1 FEVEVTK (SEQ ID NO: 31)

_HOMO Afamin precursor, p43652 LSQKFPK (SEQ ID NO: 18)

_HOMO Alpha-fetoprotein precursor, p02771 IYEIAR (SEQ ID NO: 11)

_HOMO U3 small nucleolar ribonucleoprotein protein IMP3, q9nv31 MEDFVTWVDSSK (SEQ ID NO: 41)

_HOMO IQ domain-containing protein G, q9h095 EMNLEGTNLDKLPMAS (SEQ ID NO: 14)

_HOMO DNA-binding protein SATB1, q01826 MQNFLQLPEAERDR (SEQ ID NO: 54)

_HOMO Regulatory-associated protein of mTOR, q8n122 YYDGFMGQRVGAISCLAFHPHWPHLAVGSND (SEQ ID NO: 62)

_HOMO Rho GTPase-activating protein 29, q52Iw3 VVDQGCFPK (SEQ ID NO: 57)

Stage I (complex 7)

_HOMO Serum albumin, a6nbz8 (24 fragments)

_HOMO A-kinase anchor protein 13 (AKAP 13) (Breast cancer nuclear receptor-binding auxiliary protein) q12802 VGPVSLPR (SEQ ID NO: 3)

_HOMO Cleavage stimulation factor 64 kDa subunit, p33240-2 ATEEQLK (SEQ ID NO: 4)

_HOMO Heat shock 105 kDa/110 kDa protein 1, q5tbm7 SVNEVMEWMNNVMNAQ (SEQ ID NO: 42)

_HOMO Dynein heavy chain 8, axonemal, q96jb1 FEVEVTK (SEQ ID NO: 31)

_HOMO Afamin precursor, p43652 LSQKFPK (SEQ ID NO: 18)

TABLE 4-continued

Mass spectrophotometric analysis of components of Stage I complexes

_HOMO DNA-binding protein SATB1, q01826 MQNFLQLPEAERDR (SEQ ID NO: 54)

_HOMO Peptidyl-prolyl cis-trans isomerase, q8n1e6 QITDSSLGRIAQ (SEQ ID NO: 56)

_HOMO Alpha-fetoprotein precursor, p02771 IYEIAR (SEQ ID NO: 11)

_HOMO Peroxiredoxin 3 isoform a variant, q53hc2 LLSDLTK (SEQ ID NO: 63)

_HOMO Cadherin EGF LAG seven-pass G-type receptor 2 precursor, q9hcu4 DAGTELTGHLVP (SEQ ID NO: 64)

_HOMO Nuclear receptor corepressor 2, upi00015dff7a LQAGVMASPPPP (SEQ ID NO: 65)

_HOMO SH2B adaptor protein 2, upi000022d3dd TELSCTRGGCLASR (SEQ ID NO: 45)

_HOMO Vacuolar protein-sorting-associated protein 36, q86vn1 DGEEKIK (SEQ ID NO: 46)

Stage I (Comglex 8)

_HOMO Serum albumin, a6nbz8 (24 fragments)

_HOMO A-kinase anchor protein 13 (AKAP 13) (Breast cancer nuclear receptor-binding auxiliary protein) q12802 VVGPVSLPR (SEQ ID NO: 66)

_HOMO Cleavage stimulation factor 64 kDa subunit, p33240-2 ATEEQLK (SEQ ID NO: 4)

_HOMO Golgi reassembly-stacking protein 2, q9h8y8 TPVSEK (SEQ ID NO: 5)

_HOMO Afamin precursor, p43652 LSQKFPK (SEQ ID NO: 18)

_HOMO Alpha-fetoprotein precursor, p02771 IYEIAR (SEQ ID NO: 11)

_HOMO U3 small nucleolar ribonucleoprotein protein IMP3, q9nv31 MEDFVTWVDSSK (SEQ ID NO: 41)

_HOMO IQ domain-containing protein G, q9h095 EMNLEGTNLDKLPMAS (SEQ ID NO: 14)

_HOMO DNA-binding protein SATB1, q01826 MQNFLQLPEAERDR (SEQ ID NO: 54)

_HOMO Peptidyl-prolyl cis-trans isomerase, q8n1e6 QITDSSLGRIAQ (SEQ ID NO: 56)

_HOMO Rho GTPase-activating protein 29, q52Iw3 VVDQGCFPK (SEQ ID NO: 57)

_HOMO Vacuolar protein-sorting-associated protein 36, q86vn1 DGEEKIK (SEQ ID NO: 46)

_HOMO Cadherin EGF LAG seven-pass G-type receptor 2 precursor, q9hcu4 DAGTELTGHLVP (SEQ ID NO: 64)

Table 5 shows the new cancer peptide motifs (with their amino acid sequences) from Stage I breast cancer complexes.

TABLE 5

List of cancer peptide motifs from Stage I breast cancer complexes

1) Dermcidin precursor (Preproteolysin) (ENAGEDPGLAR (SEQ ID NO: 9)), (LGKDAVEDLESVGK (SEQ ID NO: 10)), (DAVEDLESVGK (SEQ ID NO: 27)), (YDPEAASAPGSGNPCHEASAAQK (SEQ ID NO: 28)) and (GAVHDVKDVLDSV (SEQ ID NO: 29))

2) A-kinase anchor protein 13 (VGPVSLPR (SEQ ID NO: 3))

3) Cleavage stimulation factor 64 kDa subunit (ATEEQLK (SEQ ID NO: 4))

TABLE 5-continued

List of cancer peptide motifs from Stage I breast cancer complexes

4) Heat shock 105 kDa/110 kDa protein 1 (SVNEVMEWMNNVMNAQ (SEQ ID NO: 42))

5) KIAA0861 protein (LATAELPR (SEQ ID NO: 43))

6) DNA-binding protein SATB1 (MQNFLQLPEAERDR (SEQ ID NO: 54))

7) Regulatory-associated protein of mTOR (YYDGFMGQRVGAISCLAFHPHWPHLAVGSND (SEQ ID NO: 62))

8) BRCA1 associated RING domain 1 (ELAVILK (SEQ ID NO: 59))

9) G-protein coupled receptor-associated sorting protein 1 (EEASPEAVAGVGFESK (SEQ ID NO: 44))

10) Vacuolar protein-sorting-associated protein 36 (DGEEKIK (SEQ ID NO: 46))

11) Rho GTPase-activating protein 29 (VVDQGCFPK (SEQ ID NO: 57))

12) E3 ubiquitin-protein ligase BRE1B, o75150 (EGPSLGPPP (SEQ ID NO: 47))

13) Zinc finger protein ubi-d4 (GAPDPRVDDDSLGEFPVTN (SEQ ID NO: 67))

14) Isoform 2 of O60449 (GADMISIHNEEENAFILDTLK (SEQ ID NO: 50))

15) Docking protein 3 (Downstream of tyrosine kinase 3) (GPALLVLGPDAIQLR (SEQ ID NO: 51))

16) Zinc finger CCCH domain-containing protein 4 (ASPSGDASPPATAPYDPR (SEQ ID NO: 60))

17) Cadherin EGF LAG seven-pass G-type receptor 2 precursor (DAGTELTGHLVP (SEQ ID NO: 64))

18) RNA U small nuclear RNA export adapter protein (GILGMEGTIDR (SEQ ID NO: 68))

19) Nuclear receptor corepressor 2 (LQAGVMASPPPP (SEQ ID NO: 65))

20) SH2B adaptor protein 2 (TELSCTRGGCLASR (SEQ ID NO: 45))

21) Peptidyl-prolyl cis-trans isomerase (QITDSSLGRIAQ (SEQ ID NO: 56))

22) Ubiquitin carboxyl-terminal hydrolase, a2rue3 (PDGASCQGQPALHSENPFAKANGLPGK (SEQ ID NO: 58))

23) U3 small nucleolar ribonucleoprotein protein IMP3 (MEDFVTWVDSSK (SEQ ID NO: 41))

24) Peroxisomal proliferator-activated receptor A interacting complex 285 (FAPSVVQ (SEQ ID NO: 52))

We have identified cancer peptide motifs from other Stage I serum albumin complexes. In addition, we have identified 50 cancer peptide motifs from some of the Stage II breast cancer complexes. Table 6 list the amino acid sequence of the new cancer peptide motifs from these cancer complexes.

TABLE 6

List of new cancer peptide motifs from other Stage I, and Stage II breast cancer complexes _HOMO E1A binding protein p300 upi00001ae876 VAQGMGSGAHTADPEK (SEQ ID NO: 69)

_HOMO DNA excision repair protein ERCC-6 url h_q03468 GAEVNAVTSNRSDPLKDDPHMSSN (SEQ ID NO: 70)

_HOMO Peptidylprolyl isomerase domain and WD repeat-containing protein 1 q96bp3 IATIGSDR (SEQ ID NO: 71)

TABLE 6-continued

List of new cancer peptide motifs from other Stage I, and
Stage II breast cancer complexes _HOMO Zinc finger MYM-type protein 6 o95789 SSQSSQPSRLLK (SEQ ID NO: 72)

_HOMO Mitogen-activated protein kinase kinase kinase 1 q13233 DEESLTVCEDGCRNK (SEQ ID NO: 73)

_HOMO Macrophage-stimulating protein receptor precursor (EC 2.7.10.1) upi000013e344 LFASGDQVFQVPIQGPGCR (SEQ ID NO: 74)

_HOMO Spindle and kinetochore-associated protein 1 q96bd8 ILHQPKKSMNSVTR (SEQ ID NO: 75)

_HOMO mucin 17 upi0000d626c2 TPVDTK (SEQ ID NO: 76)

_HOMO Docking protein 3 (Downstream of tyrosine kinase 3) upi0000d616c3 GPALLVLGPDAIQLR (SEQ ID NO: 51)

_HOMO Tripartite motif-containing protein 32 q13049 PKGGGYSVLIR (SEQ ID NO: 49)

_HOMO Histone acetyltransferase PCAF q92831 DKLPLEK (SEQ ID NO: 77)

_HOMO Zinc finger CCCH domain-containing protein 4 q9upt8 ASPSGDASPPATAPYDPR (SEQ ID NO: 60)

_HOMO Nuclear receptor subfamily 0 group B member 2 q96s05 QGQPVVPP (SEQ ID NO: 78)

_HOMO Regulatory-associated protein of mTOR (Raptor) (P150 target of rapamycin (TOR)-scaffold protein) q8n122 YYDGFMGQRVGAISCLAFHPHWPHLAVGSND (SEQ ID NO: 62)

_HOMO FERM and PDZ domain-containing protein 3 q5jv73 SSRCTPPPADSELVSFCYLHMR (SEQ ID NO: 79)

_HOMO Multiple EGF-like-domains 8 a8kay0 RKGDAACSR (SEQ ID NO: 80)

_HOMO Protein GREB1 q4zg55 LVYDMVVSTDSSGLPKAASLLP (SEQ ID NO: 81)

_HOMO Dedicator of cytokinesis protein 3 (Modifier of cell adhesion) (Presenilin-binding protein) (PBP) upi0000d61b10 GEETENKKIGCTVNLMNFYK (SEQ ID NO: 82)

_HOMO Histone deacetylase 7a q8wui4 + 1 LAEVILK (SEQ ID NO: 83)

_HOMO DNA repair protein RAD52 homolog p43351 LEVDLTK (SEQ ID NO: 84)

_HOMO Ras and Rab interactor 2 q8wyp3 TCARDSGYDSL (SEQ ID NO: 85)

_HOMO PDZ domain-containing protein 2 (PDZ domain-containing protein 3) o15018 PPETSSKGSDSELKK (SEQ ID NO: 86)

_HOMO Histone deacetylase inducible gi|20306864 PATVQSR (SEQ ID NO: 87)

_HOMO cDNA FLJ77425, highly similar to *Homo sapiens* peroxisome proliferative activated receptor, delta (PPARD), transcript variant 1, mRNA a8k6j6 ELTEFAK (SEQ ID NO: 88)

_HOMO Mucin-16 q8wxi7 LVITIDR (SEQ ID NO: 89)

_HOMO T-cell lymphoma invasion and metastasis 2 q5vya4 STSPGKYPHPGLADFADNLIK (SEQ ID NO: 90)

_HOMO FERM and PDZ domain-containing protein 1 q5syb0 HREAAGN (SEQ ID NO: 91)

_HOMO Plexin-B3 precursor upi0001662789 TDFVQMAVL (SEQ ID NO: 92)

_HOMO Endoplasmic reticulum resident protein ERp27 precursor q96dn0 EIPAVPILHSMVQK (SEQ ID NO: 93)

_HOMO VPS10 domain-containing receptor SorCS2 precursor upi00015e0762 LLQERVTKDHVFWSVSGVDADPDLVHVEAQDLGGDFR (SEQ ID NO: 94)

_HOMO Cancer/testis antigen 47.13 ur1h_p0c2w7 RYPAAGIGFVFL (SEQ ID NO: 95)

TABLE 6-continued

List of new cancer peptide motifs from other Stage I, and
Stage II breast cancer complexes _HOMO Islet cell autoantigen 1 (69 kDa islet cell autoantigen)
upi00015e0457
DVSQELDPDLYKQ (SEQ ID NO: 96)

_HOMO Kinesin-like protein KIF9 upi000012de55 YENKGLMIIDEEEFLL (SEQ ID
NO: 97)

_HOMO Protein transport protein Sec23B q15437 IYACALDQTGLLEMK (SEQ ID
NO: 98)

_HOMO Protein transport protein Sec24B (SEC24-related protein B).
upi00001ae8ce VITSNTIVR (SEQ ID NO: 99)

_HOMO PRP18 pre-mRNA processing factor 18 homolog q5t9p7
DMDIITKFLKFLLGVWAKELNAR (SEQ ID NO: 100)

_HOMO NudC domain-containing protein 2 q8wvj2 KLFDSTIADEGTWTLEDRK
(SEQ ID NO: 101)

_HOMO Sorting nexin-12. upi0000d61d89 CLHMFLQE (SEQ ID NO: 102)

_HOMO Ubiquitin-protein ligase E3B q7z3v4 PELQRLISGDNAEIDLEDLK (SEQ ID
NO: 103)

_HOMO Ret finger protein-like 2 o75678 MEVAELGFPETAVSQ (SEQ ID NO: 104)

_HOMO Centromere protein L q8n0s6 MDHYVATTEFLWSVPCSPQS (SEQ ID NO:
105)

_HOMO DNA-repair protein XRCC3 o43542 RLTNLSS (SEQ ID NO: 106)

_HOMO Peroxiredoxin 3 isoform a variant q53hc2 LLSDLTK (SEQ ID NO: 63)

_HOMO Ubiquitin carboxyl-terminal hydrolase q05c98
QGLPGTSNSNSSRSGSQR (SEQ ID NO: 20)

_HOMO RNA U small nuclear RNA export adapter protein q9h814 ILGMEGTIDR
(SEQ ID NO: 61)

_HOMO E3 SUMO-protein ligase RanBP2 p49792
SDTTIKPNPENTGPTLEWDNYDLR (SEQ ID NO: 107)

_HOMO Cell cycle related kinase o95137 QYVVQLK (SEQ ID NO: 108)

_HOMO Dedicator of cytokinesis protein 8 q8nf50 EFVEVIK (SEQ ID NO: 109)

_HOMO Annexin A13 p27216 IEEETSGDLQK (SEQ ID NO: 110)

_HOMO vacuolar protein sorting 13D isoform 1 upi0000451ca9
MYERYSLSFMDLQIMVGRV (SEQ ID NO: 111)

_HOMO E3 ubiquitin-protein ligase RNF19B q6zmz0 VRTKHTSGLSYGQES (SEQ ID
NO: 112)

_HOMO AP-2 complex subunit alpha-1 (Adapter-related protein complex 2
alpha-1 subunit) (Alpha-adaptin A) (Adaptor protein complex AP-2 alpha-1
subunit) (Clathrin assembly protein complex 2 alpha-A large chain) (100 kDa
coated vesicle protein A) upi00015df9e1 GGAQVQQVLNIECLRDFLTPPLLSVR
(SEQ ID NO: 113)

_HOMO RNA-binding protein with multiple splicing 2 q6zry4
AGAEAAKNALNGIRFDPENPQT (SEQ ID NO: 114)

_HOMO EGF-like module-containing mucin-like hormone receptor-like 4
precursor (G-protein coupled receptor 127) upi00015df8ba
ESTAVALSLINLLGILPIQNTSTSLH (SEQ ID NO: 115)

_HOMO Tyrosine-protein kinase receptor q17rw0 MAHGDLK (SEQ ID NO: 116)

_HOMO RAD50 protein q32p42 MSRIEKMSILGVRSFGIEDK (SEQ ID NO: 117)

_HOMO Transcriptional adapter 2-beta q86tj2 LAEVSPLR (SEQ ID NO: 22)

_HOMO Jun dimerization protein 2 q8wyk2 TEFLQRESERLELMN (SEQ ID NO:
118)

TABLE 6-continued

List of new cancer peptide motifs from other Stage I, and
Stage II breast cancer complexes _HOMO RABEP1 protein q05bx6 VKELNHYLEAEKSCRTDL (SEQ ID NO: 119)

_HOMO EP300-interacting inhibitor of differentiation 1 q9y6b2
EPALDGGFQMHYEKTPFDQLAFIEELFSL (SEQ ID NO: 120)

_HOMO Cancer antigen 1 q5tam2 SDAEHFK (SEQ ID NO: 121)

_HOMO Exportin-2 (Exp2) (Importin-alpha re-exporter) (Chromosome
segregation 1-like protein) (Cellular apoptosis susceptibility protein)
upi00015df899 LLTEMVNR (SEQ ID NO: 122)

Example 5

Validation of Identified Cancer Peptide Motifs from Both Stage 0 and Stage I Breast Cancer Six cancer peptide motifs from Stage 0 and Stage I breast cancer complexes were chosen for analysis. Polypeptides containing the above amino acid sequence were synthesized. Due to the nature of tryptic digestion, the length of amino acid residues present in the cancer complexes is likely to be longer than the indicated sequence. To increase specificity of detection, the optimal polypeptide length should be around 14 to 20 amino acid residues, although longer or even shorter polypeptides may be used. Accordingly, some of these cancer peptide motifs with less than the optimal length were elongated from the carboxyl and/or amino terminal ends. The synthesized polypeptides were subsequently injected into rabbits to produce antibodies. Table 7 shows the six cancer peptide motifs followed by their respective synthesized peptide sequences if any.

Antibody) was found to be a tumor suppressor protein. The antibody against G-protein coupled receptor-associated sorting protein 1 (Biomarker 4, corresponding to residues 850-865 of the 1,395 amino acid protein GASP-1) (anti-EEAS-PEAVAGVGFESK) (Biomarker 4 Antibody) and the antibody against Vacuolar protein-sorting-associated protein 36 (Biomarker 6, corresponding to residues 26-38 of the 386 amino acid protein) (anti-GVRIYDGEEKIKFDAG) (Biomarker 6 Antibody) were further validated to be specific for cancers and shown to be new targets for cancer therapeutics that inhibit growth and invasion of tumors.

Figure 7:
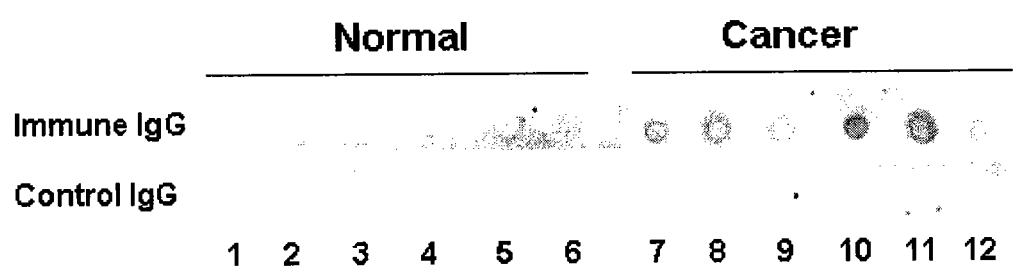
FIG. 7 shows detection of Biomarker 4 (EEASPEAVAGVGFESK; SEQ ID NO: 44) in serum samples from six healthy volunteers (lanes 1-2: men; lanes 3-6: women) and six women with ductal carcinoma (lanes 7-12) with a rabbit antibody against Biomarker 4 ("Biomarker 4 Antibody") in a Dot Blot analysis.

In further dot blot experiments, Biomarker 4 Antibody was used to detect Biomarker 4 in serum samples from six healthy individuals (lane 1-2, men; lanes 3-6: women) and six women with ductal carcinoma (lanes 7-12) (FIG. 7). Biomarker 4 was found highly expressed only in cancer patients.

In Western blot analysis, G-protein coupled receptor-associated sorting protein 1 (GASP-1) was detected by Biomarker 4 Antibody as being highly expressed in all of the seven breast

TABLE 7

Selection of cancer peptide modifs for analysis

Stage 0

Biomarker 1: G2/M phase-specific E3 ubiquitin-protein ligase (NLSLNS (SEQ ID
NO: 30)), SLSKNLSLNSQALK (SEQ ID NO: 123)

Biomarker 2: Zinc finger CCCH domain-containing protein 11A (IDSEIK (SEQ ID
NO: 8)), CIKLKIDSEIKKTVVL (SEQ ID NO: 124)

Biomarker 3: cDNA FLJ76883, highly similar to FKSG44 gene (DSEGTPVNK (SEQ
ID NO: 23)), DGDSEGTPVNKLLK (SEQ ID NO: 125)

Stage I

Biomarker 4: G-protein coupled receptor-associated sorting protein 1
(EEASPEAVAGVGFESK (SEQ ID NO: 44))

Biomarker 5: Rho GTPase-activating protein 29 (VVDQGCFPK (SEQ ID NO: 57)),
CSIGVVDQGCFPKPLL (SEQ ID NO: 126)

Biomarker 6: Vacuolar protein-sorting-associated protein 36 (DGEEKIK (SEQ ID
NO: 46)), GVRIYDGEEKIKFDAG (SEQ ID NO: 127)

Figure 8:
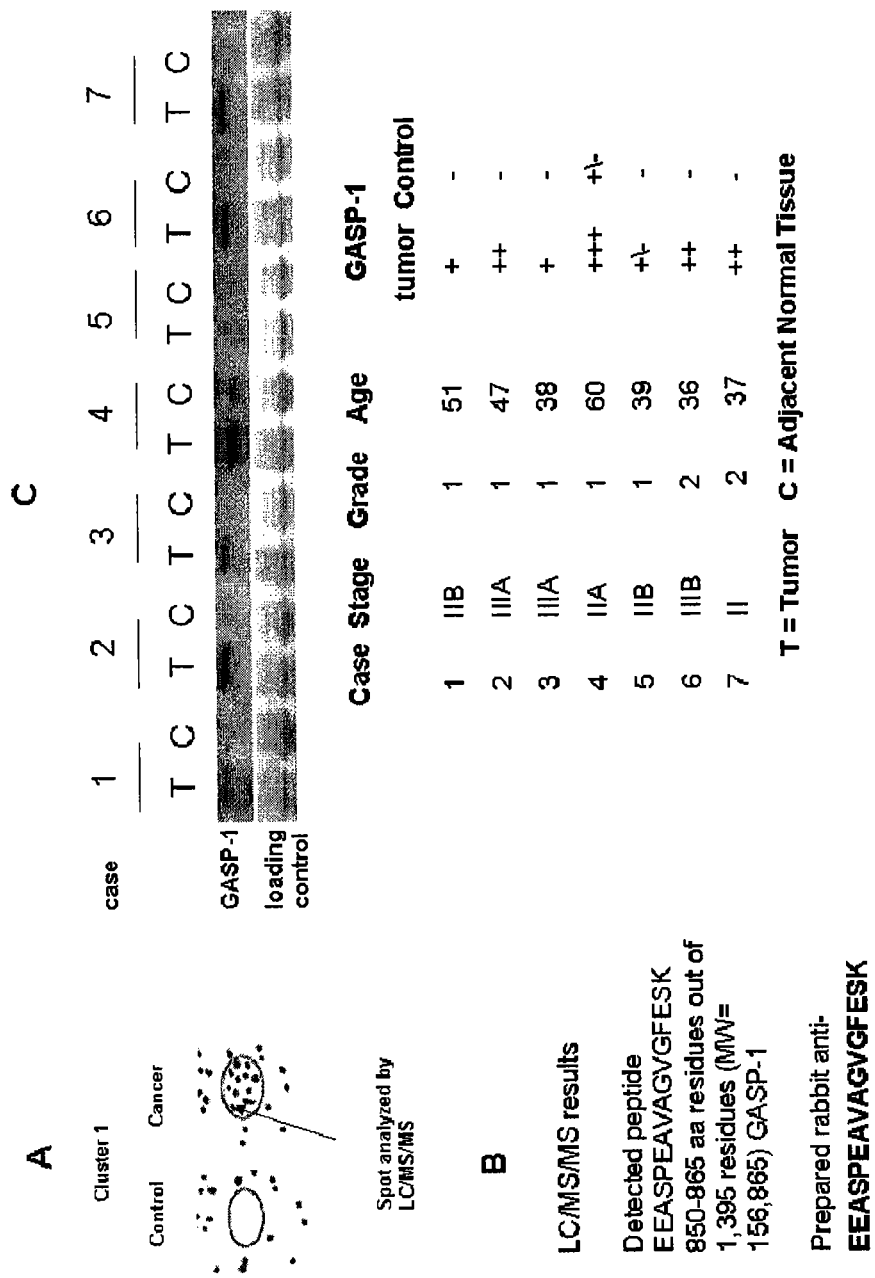
FIG. 8A-8C show the expression of GASP-1 in Stage-specific breast cancer. (A) shows the protein spot in Cluster 1 selected for LC/MS/MS analysis. (B) shows that the detected peptide ((EEASPEAVAGVGFESK; SEQ ID NO: 44; Biomarker 4) correlates with residues 850-865 of GASP-1. (C) shows western blot (NSTA-Blot breast tissue blots obtained commercially from ImGenex) containing SDS-PAGE resolved proteins from tumor tissues (T) and adjacent normal tissues (C) in seven cases of stage II or stage III breast cancer. GASP-1 was detected by Biomarker 4 Antibody. Loading controls represent stained actin bands.

In dot blot experiments, serum samples from breast cancer patients and normal individuals were spotted on a membrane and detected with antibodies generated against Biomarkers 1-6. All six antibodies showed a 3 to 10-fold over-expression in sera from breast cancer patients when compared to sera from the normal individuals. The antibody against cDNA FLJ76883 which is highly similar to FKSG44 gene (Biomarker 3, corresponding to residues 305-318 of the 464 amino acid protein) (anti-DGDSEGTPVNKLLK) (Biomarker 3 cancer patients of Stage II or Stage III (FIG. 8C). More importantly, GASP-1 is only expressed in the tumor cells (T) but not in the adjacent normal cells (C) from the same patients.

Figure 9:
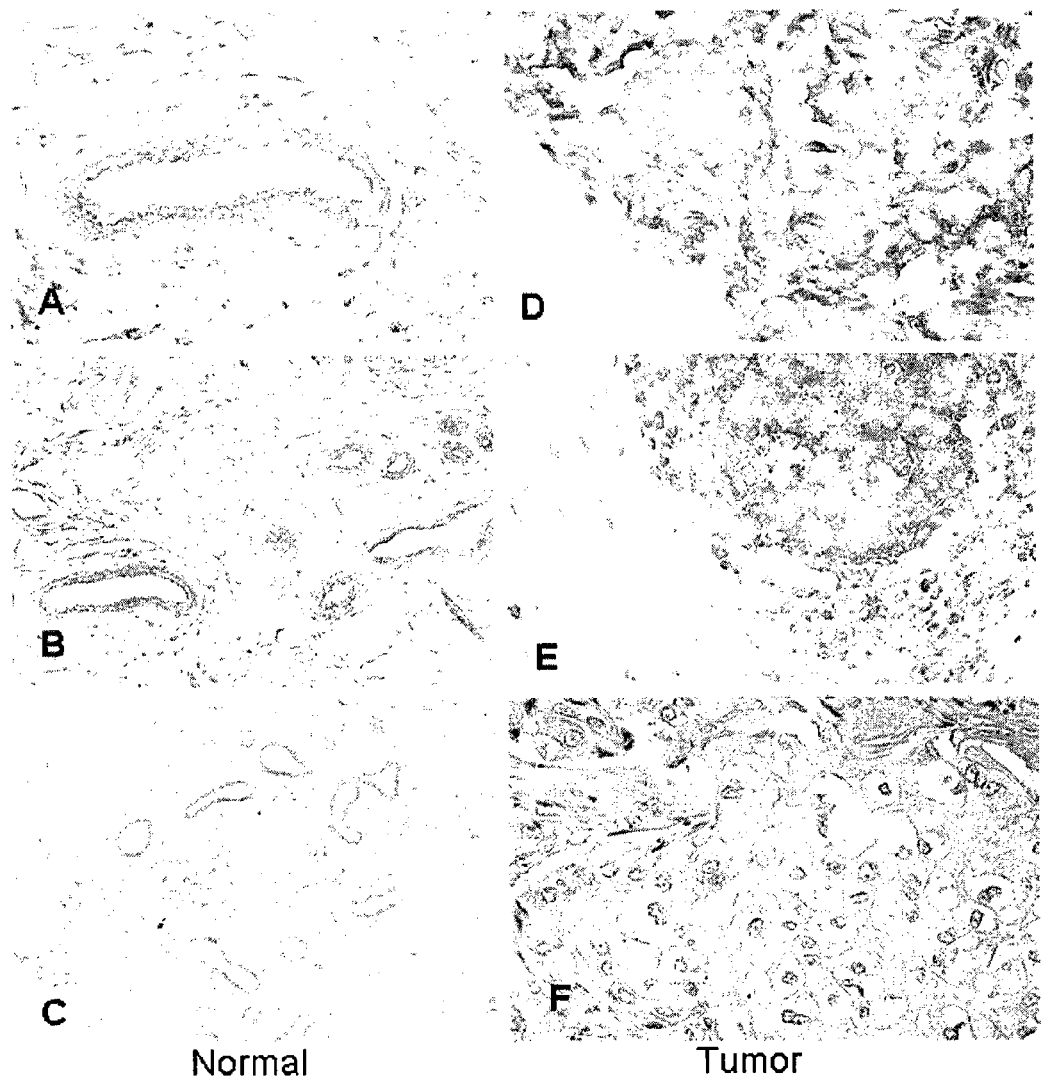
FIGS. 9A-9F show immunohistochemical staining of normal breast tissues (A-C) and invasive ductal carcinoma (D-F) with Biomarker 4 Antibody.

Expression of GSAP-1 protein in tumor cells was examined by immunohistochemical staining of a normal breast tissue (FIG. 9A-9C) and invasive ductal carcinoma (FIG. 9D-9F) with Biomarker 4 Antibody. GASP-1 was highly expressed in the tumor cells.

Figure 10:
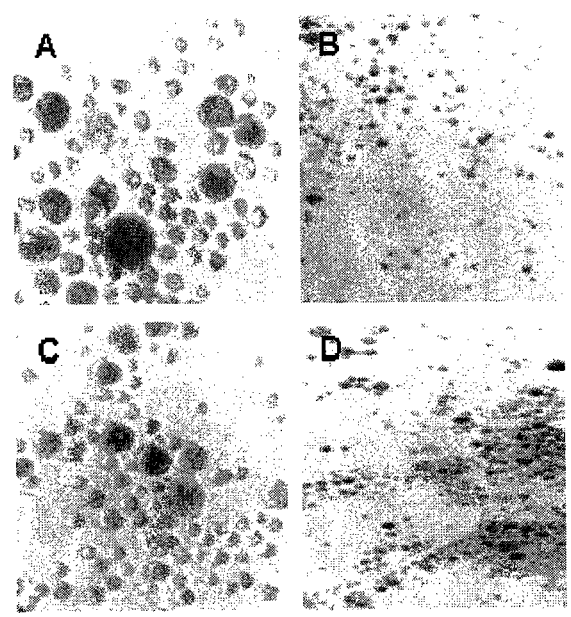
FIGS. 10A-10D show proliferation of MDA-MB-231 breast carcinoma cells in soft agar containing (A) no treatment, (B) a rabbit antibody against Biomarker 4 (EEASPEAVAGVGFESK; SEQ ID NO: 44) ("Biomarker 4 Antibody), (C) control IgG, or (D) a rabbit antibody against Biomarker 6 (GVRIYDGEEKIKFDAG; SEQ ID NO: 127) ("Biomarker 6 Antibody").

Proliferation of MDA-MB-231 Breast carcinoma cells in soft agar was observed two weeks after the cells were introduced into the soft agar containing no treatment (FIG. 10A), 10 µg/ml Biomarker 4 Antibody (FIG. 10B), 10 µg/ml control IgG (FIG. 10C) and 10 µg/ml Biomarker 6 Antibody (FIG. 10D). Both Biomarker 4 Antibody and Biomarker 6 Antibody inhibited dramatically the growth of MDA-MB-231 Breast carcinoma in soft agar (FIG. 10). In contrast, control IgG had no effect on tumor cell growth.

Figure 11:
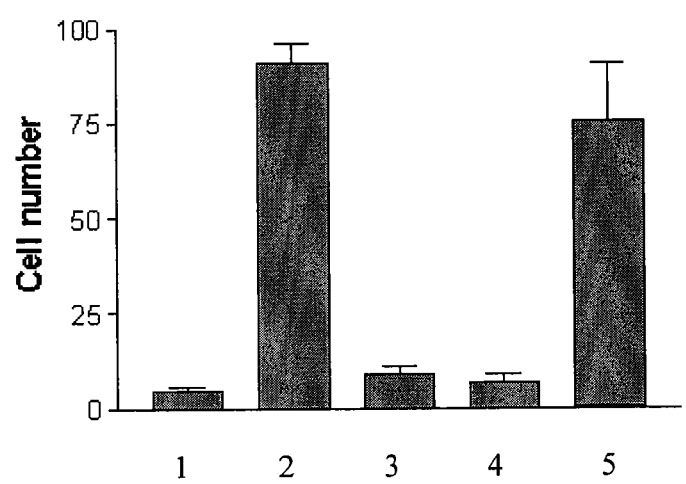
FIG. 11 shows adhesion of MDA-MB-231 breast carcinoma cells to plates coated with (1) no treatment, (2) fibronectin, (3) control IgG, (4) Biomarker 4 Antibody, or (5) Biomarker 6 Antibody.

In a cell adhesion assay, MDA-MB-231 Breast carcinoma cells added to plates coated with (1) no treatment, (2) 2 µg/ml fibronectin, (3) 2 µg/ml control IgG, (4) 2 µg/ml Biomarker 4 Antibody, and (5) 2 µg/ml Biomarker 6 Antibody (FIG. 11). Like fibronectin, Biomarker 6 Antibody promoted cell adhesion indicating that Biomarker 6 is located on the cell surface. Biomarker 4 Antibody appeared to be internalized (FIG. 11) Antibodies that do not bind directly to cell surface epitopes are generally internalized.

Figure 12:
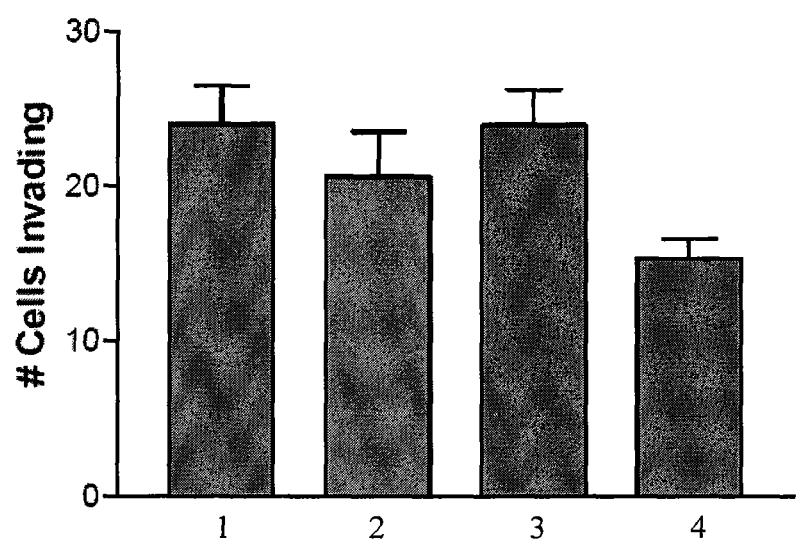
FIG. 12 shows invasion of MDA-MB-231 breast carcinoma cells into soft agar containing (1) no treatment, (2) control IgG, (3) Biomarker 4 Antibody, or (4) Biomarker 6 Antibody.

In a cell invasion assay, MDA-MB-231 Breast carcinoma cells in soft agar were counted after the cells were added to the top of soft agar containing (1) no treatment, (2) 10 µg/ml control IgG, (3) 10 µg/ml Biomarker 4 Antibody, and (4) 10 µg/ml Biomarker 6 Antibody, and cultured overnight (FIG. 12). A chemoattractant (i.e., bFGF) was placed under the agar. Biomarker 6 Antibody inhibited cancer cell migration suggesting that Biomarker 6 is located on the cell surface.

Figure 13:
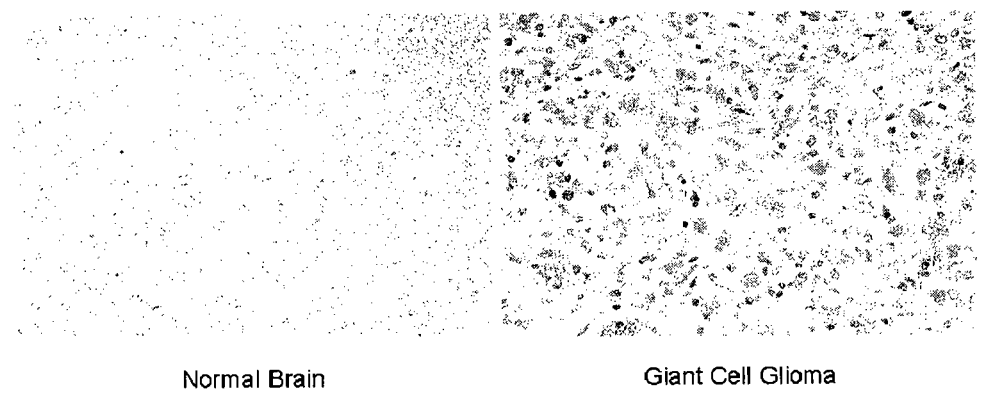
FIGS. 13A and 13B show immunohistochemical staining of normal brain (A) and glioma (B) with Biomarker 4 Antibody.

Biomarker 4 is a general cancer marker. Using immunohistochemical staining, biomarker 4 was found to be highly expressed in all 59 out of 59 cases of breast cancer and all 33 out of 33 cases of brain cancer, while corresponding normal tissues were either negative or weakly positive. It was also expressed strongly in bladder, liver, lung and other tumor tissues. Biomarker 4 was detected by Western blot analysis in MDA-MB-231 breast cancer cells grown in tissue culture and brain cancer cells, PC12 cells and primary glioblastoma cells. In brain cancer (glioma), cytoplasmic staining was very strong (FIG. 13). Table 8 lists various tumors that highly express Biomarker 4. The tumor sections were stained in a tissue array purchased from Imgenex, San Diego, Calif.

TABLE 8

Tumors stained positively with Biomarker 4 Antibody

| | |
|---|---|
| 1. | Glioma |
| 2. | Lung Squamous cell carcinoma |
| 3. | Hepatocellular carcinoma |
| 4. | Esophagus squamous cell carcinoma |
| 5. | Stomach adenocarcinoma |
| 6. | Small bowel malignant stromal tumor |
| 7. | Renal cell carcinoma |
| 8. | Infiltrating ductal breast carcinoma |
| 9. | Larynx cancer |
| 10. | Metastatic malignant melanoma |
| 11. | Mucinous cystadenocarcinoma of ovary |
| 12. | Endometrial carcinoma |
| 13. | Bladder cancer |
| 14. | Adenocarcinoma of rectum |

Example 6

Identification of Cancer Peptide Motifs of Reported Cancer Proteins

Even though several cancer protein biomarkers have been reported in the literature, their cancer peptide motifs in these proteins have not been identified. As indicated earlier, our cancer peptide motif represents only 1 to 3% of the entire cancer protein, it is therefore important to identify the small amino acid sequence representing cancer peptide motif within the large cancer protein. Using the methods of the present invention, cancer peptide motifs in these cancer proteins were identified. These new cancer peptide motifs provide not only better cancer biomarkers but also better targets for therapeutic intervention or treatment. In analysis of cancer peptide motifs from Stage 0 and early Stage I breast cancer, cancer peptide motifs have been discovered from the following reported cancer proteins: 1) Dermcidin (Porter et al., Proc. Nat'l. Acad. Sci, 100: 10931-10936, 2003), 2) A-kinase anchor protein 13 (Wirtenberger, et al., Carcinnogenesis, 27: 593-98, 2006), 3) Cleavage stimulation factor 64 kDa subunit (Watkins and Szaro U.S. Pat. No. 6,939,424), 4) Polactin-induced protein (Vonderhaar, B., Endocrine-Related Cancer 6: 389-404, 1999), 5) Mucin-like protein 1 precursor (Kim et al., Breast Cancer Research 11: R22, 2009), 6) Mucin MUC5B (Sonora et al., Histochem Cytochem, 54: 289-99, 2006), and 7) Eukaryotic translation initiation factor 4E transporter (Graff et al, Cancer Research, 68: 631, 2008). Their polypeptide motifs are as follows:

1) Dermcidin precursor (Preproteolysin) (ENAGEDPGLAR (SEQ ID NO: 9)), (LGKDAVEDLESVGK (SEQ ID NO: 10)), (DAVEDLESVGK (SEQ ID NO: 27)), (YD-PEAASAPGSGNPCHEASAAQK (SEQ ID NO: 28)), (GAVHDVKDVLDSV (SEQ ID NO: 29))
2) A-kinase anchor protein 13 (VGPVSLPR (SEQ ID NO: 3))
3) Cleavage stimulation factor 64 kDa subunit (ATEEQLK (SEQ ID NO: 4))
4) Prolactin-induced protein (TVQIAAVVDVIR (SEQ ID NO: 1)), (FYTIEILKVE (SEQ ID NO: 2))
5) Mucin-like protein 1 precursor (WVGDLPNGR (SEQ ID NO: 6))
6) Mucin MUC5B (TTPTVISWK (SEQ ID NO: 12))
7) Eukaryotic translation initiation factor 4E transporter (LSSSSVPSADR (SEQ ID NO: 19))

Analysis of all the Stage 0 complexes also revealed that serum albumin is the major anchoring protein with at least 14 detected unique fragments covering many regions of the protein, suggesting that albumin could be intact (i.e., not degraded). Furthermore, from the analysis of its fragments, it appears that serum albumin is aggregated with about 10 or more molecules present in each of the complexes.

The second most common component of the four Stage 0 albumin complexes is dermcidin with cancer complex 4 containing 12 fragments covering 75% of this protein. Cancer complexes 1 and 2 also contain multiple fragments of this protein. Dermcidin, which is produced primarily in human sweat glands, exhibits a wide range of biological functions. In addition to its antimicrobial function, it is reported to be a neuronal survival factor, a putative oncogene in breast cancer and a proteolysis-inducing factor (PIF) that induces skeletal muscle proteolysis to cause cancer cachexia (Lowrie et al., Brit. 3. Cancer, 94: 1663-1671, 2006). Association of dermcidin with serum albumin could regulate cell function by modulating the proteolytic cascades on the cell surface, and also involve in the pathophysiology and progression of breast cancer.

Another protein that is present in all 4 Stage 0 complexes is "Cleavage stimulation factor 64 kDa subunit" (CSTF2) which was reported to be a breast cancer protein by Watkins and Szaro (U.S. Pat. No. 6,939,424). CSTF2 is one of three (including CSTF1 and CSTF3) cleavage stimulation factors which combine to form CSTF which is involved in the polyadenylation and 3'-end cleavage of pre-mRNAs. Upregulation or mutation in CSTF2 may promote breast cancer growth.

Another cancer protein that is present in all Stage 0 complexes is "A-kinase anchor protein 13" (AKAP 13) which is also called "breast cancer nuclear receptor-binding auxiliary protein." The A-kinase anchor protein 13 functions by binding to the regulatory subunit of protein kinase A (PKA) and tethering the cAMP-dependent protein kinase A to its subcellular environment. Its rho GTPases activity functions as a guanine nucleotide exchange factor. Alterations within AKAP 13 are expected to provoke a constitutive rho signaling, facilitating the development of breast cancer. Interestingly only the sequence VGPVSLPR spanning residue 2,454-2,461 of the 2,881 amino acid A-kinase anchor protein 13 was detected.

The fact that all four breast cancer protein complexes contain these four proteins or their fragments suggests that possibility that they may actually function as a scaffold or platform allowing other cancer protein fragments to latch on.

Some of the proteins (or their fragments) found in Stage 0 also appear in Stage I breast cancer. All 8 newly produced Stage I albumin complexes contain multiple copies of serum albumin (10 or more copies) and peptide fragments from A-kinase anchor protein 13 and Cleavage stimulation factor 64 kDa subunit. Most of the complexes also contain peptide fragment(s) from Golgi reassembly-stacking protein 2.

Besides Dermcidin, A-kinase anchor protein 13, and Cleavage stimulation factor 64 kDa subunit, the newly identified cancer peptide motifs from other reported cancer proteins include 1) Heat shock 105 kDa/110 kDa protein 1 (Hosaka S, Cancer Sci. 97: 623-632, 2006), 2) KIAA0861 (WO/2005/118856), 3) DNA-binding protein SATB1 (T. Kohwi-Shigematsu, the Medical News, Mar. 13, 2008), 4) Regulatory-associated protein of mTOR (RINI, B., Clinical Cancer Research 14, 1286, Mar. 1, 2008), and 5) BRCA1 associated RING domain 1 (Ghimenti C., Breast Cancer Res 2000, 2(Suppl 1):P1.15). The newly identified cancer peptide motifs are as follows:
1) Heat shock 105 kDa/110 kDa protein 1 (SVNEVMEWMNNVMNAQ (SEQ ID NO: 42))
2) KIAA0861 protein (LATAELPR (SEQ ID NO: 43))
3) DNA-binding protein SATB1 (MQNFLQLPEAERDR (SEQ ID NO: 54))
4) Regulatory-associated protein of mTOR (YYDGFMGQRVGAISCLAFHPHWPHLAVGSND (SEQ ID NO: 62))
5) BRCA1 associated RING domain 1 (ELAVILK (SEQ ID NO: 59))

Example 7

Utilities of the Newly Identified Stage-Specific Breast Cancer Markers

ELISA-type diagnostic kits for detection of early stage breast cancer (Stage 0 and Stage I) will be developed. New cancer markers(s) will be selected from each stage of breast cancer for production of Stage-specific diagnostic kits. Because of the ability to detect the earliest change in breast tissue, ELISA-type diagnostic kits for newly discovered Stage 0 and Stage I breast cancer proteins will be developed first. These kits are particularly suitable for women with dense breasts that are likely to be missed by mammography, for young women who do not have access to mammography, and for high-risk women needing an interval screening between annual mammography. If necessary, diagnostic kits for other stages will be developed later.

Sandwich capture ELISA's employing two antibodies will be developed. The first capture antibody will be a polyclonal with high affinity and the second detection antibody will be either a monoclonal or polyclonal that recognizes different epitopes of the cancer maker. To amplify the signal we propose to biotinylate the second detection antibody.

Polyclonal antibodies can be produced against the newly discovered peptide fragments listed in Tables 2 and 3 (for Stage 0 breast cancer) or Tables 5 and 6 (for Stage 1 breast cancer) to develop "sandwich capture ELISAs" for detecting the presence of cancer markers. If the peptide sequence is long enough "sandwich capture ELISA" uses two antibodies against the same marker protein will be developed. The first antibody (capture antibody) on a support is a polyclonal with high affinity for one region of the peptide and the second antibody (detection antibody) that recognizes a different epitope of the same peptide.

When dealing with serum albumin complexes containing different cancer fragments, a modified sandwich capture ELISA will most likely be even more effective. The capture antibody will be a polyclonal antibody against peptide fragment from one peptide marker and the detection antibody will be a polyclonal antibody against a marker from a different protein of the same serum complex. Because the polyclonal antibodies are raised against the peptide fragments and not to the whole protein, they will be very specific and not cross react with any other protein in the body. Also, since the fragment is present only in cancer cases, it should not show up in the normal serum and hence the antibody will only react with cancer protein and not the normal protein.

Figure 14:
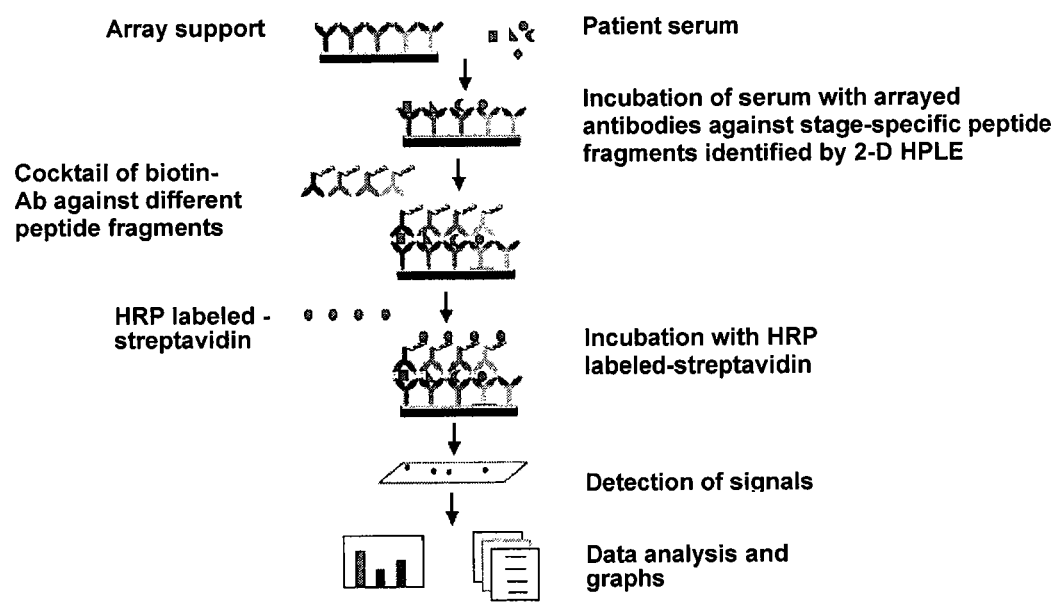
FIG. 14 shows one embodiment of an antibody array for detecting cancer-associated proteins.

The fact that many Stage-specific albumin complexes were found to have different cancer fragments on them opens up an interesting possibility of developing an antibody array that allows the detection of many cancer markers on a single array. The principle of the antibody array is illustrated in FIG. 14.

It is likely that more than one marker identified by 2-D HPLE will show a positive correlation with stage specific breast cancer. By combining these markers, it is anticipated that a stronger statistically predicative diagnostic correlation will be observed. Therefore, antibody arrays consisting of several antibodies to stage specific markers identified by 2-D HPLE spotted on each array will be developed. Production of these antibody arrays will be accomplished commercially in collaboration with companies such as RayBiotech. These arrays can be created on glass or PVDF membrane and the results quantified on x-ray films or fluorescent ELISA readers.

The present invention is not limited to the embodiments described and exemplified above, but is capable of variation and modification within the scope and range of equivalents of the appended claims.

What is claimed:

1. A method of detecting a low copy number polypeptide sequestered by serum albumin in a biological sample, comprising
   (a) obtaining the biological sample comprising a plurality of serum albumin complexes;
   (b) separating the serum albumin complexes on a membrane by a two-dimensional membrane electrophoresis;
   (c) digesting at least one separated serum albumin complex on the membrane with a protease; and
   (d) detecting the low copy number polypeptide sequestered by serum albumin in the digested complex.

2. The method of claim 1, wherein the polypeptide comprises a cancer peptide motif having an amino acid sequence selected from SEQ ID NOs: 1-122.

3. The method of claim 1, further comprising determining the amino acid sequence of the detected polypeptide.

4. A method of diagnosing a disease in a test subject, comprising
   (a) obtaining a biological sample comprising a plurality of serum albumin complexes from the test subject;
   (b) detecting one or more low copy number polypeptides sequestered by serum albumin in the biological sample in accordance with the method of claim 1 to generate a test separation profile;
   (c) providing a reference separation profile representing the disease; and
   (d) comparing the test separation profile with the reference separation profile to determine whether there is a substantial similarity between the test separation profile and the reference separation profile, wherein the substantial similarity indicates that the test subject has the disease.

5. The method of claim 4, wherein at least one of the serum albumin complexes is a breast cancer complex selected from the group consisting of Stage 0 Complexes, Stage I Complexes, Stage II Complexes, Stage III Complexes and Stage IV Complexes.

6. The method of claim 5, wherein the breast cancer complex comprises a cancer polypeptide comprising a cancer peptide motif having an amino acid sequence selected from SEQ ID NOs: 1-122.

7. The method of claim 4, wherein the disease is selected from the group consisting of cancer, a neurological disease, an autoimmune disease, and a heart disease.

8. The method of claim 7, wherein the cancer is selected from the group consisting of adenocarcinoma of rectum, bladder cancer, breast cancer, colon cancer, endometrial carcinoma, esophagus squamous cell carcinoma, glioma, hepatocellular carcinoma, infiltrating ductal breast carcinoma, larynx cancer, lung squamous cell carcinoma, melanoma, mucinous cystadenocarcinoma of ovary, pancreatic cancer, prostate cancer, renal cell carcinoma, small bowel malignant stromal tumor, and stomach adenocarcinoma.

9. The method of claim 4, wherein the comparing step is performed on a computer.

10. The method of claim 4, further comprising treating the test subject having the disease with a therapy suitable for treating the disease or the specific stage of cancer.

11. The method of claim 10, wherein the therapy comprises administering to the test subject a biomolecule having high affinity for a cancer polypeptide comprising a cancer peptide motif having an amino acid sequence selected from SEQ ID NOs:1-122.

12. The method of claim 11, wherein the biomolecule is an antibody.

13. The method of claim 8, wherein the cancer is breast cancer.

* * * * *